US011635736B2

(12) United States Patent
Kaifosh et al.

(10) Patent No.: US 11,635,736 B2
(45) Date of Patent: *Apr. 25, 2023

(54) SYSTEMS AND METHODS FOR IDENTIFYING BIOLOGICAL STRUCTURES ASSOCIATED WITH NEUROMUSCULAR SOURCE SIGNALS

(71) Applicant: META PLATFORMS TECHNOLOGIES, LLC, Menlo Park, CA (US)

(72) Inventors: Patrick Kaifosh, New York, NY (US); Tudor Giurgica-Tiron, New York, NY (US); Timothy Machado, Palo Alto, CA (US); Thomas Reardon, New York, NY (US); Erik Schomburg, Brooklyn, NY (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1062 days.

This patent is subject to a terminal disclaimer.

(21) Appl. No.: 16/165,806

(22) Filed: Oct. 19, 2018

(65) Prior Publication Data

US 2019/0121305 A1     Apr. 25, 2019

Related U.S. Application Data

(60) Provisional application No. 62/574,496, filed on Oct. 19, 2017.

(51) Int. Cl.
*A61B 5/389* (2021.01)
*G05B 13/04* (2006.01)
(Continued)

(52) U.S. Cl.
CPC .......... *G05B 13/048* (2013.01); *A61B 5/1107* (2013.01); *A61B 5/389* (2021.01);
(Continued)

(58) Field of Classification Search
CPC .............................. G05B 13/048; A61B 5/389
(Continued)

(56) References Cited

U.S. PATENT DOCUMENTS

| 1,411,995 A | 4/1922 | Dull |
| 3,408,133 A | 10/1968 | Lee |

(Continued)

FOREIGN PATENT DOCUMENTS

| CA | 2902045 A1 | 8/2014 |
| CA | 2921954 A1 | 2/2015 |

(Continued)

OTHER PUBLICATIONS

Extended European Search Report for European Application No. 18869441.8, dated Nov. 17, 2020, 20 Pages.

(Continued)

*Primary Examiner* — Nadia A Mahmood
(74) *Attorney, Agent, or Firm* — Greenberg Traurig, LLP

(57) ABSTRACT

A system comprising a plurality of neuromuscular sensors, each of which is configured to record a time-series of neuromuscular signals from a surface of a user's body; and at least one computer hardware processor programmed to perform: applying a source separation technique to the time series of neuromuscular signals recorded by the plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

19 Claims, 10 Drawing Sheets

(51) Int. Cl.
  *G06K 9/00* (2022.01)
  *G06F 3/01* (2006.01)
  *G05B 13/02* (2006.01)
  *A61B 7/00* (2006.01)
  *A61B 5/11* (2006.01)
  *A61B 5/00* (2006.01)
  *G06K 9/62* (2022.01)

(52) U.S. Cl.
  CPC ............ *A61B 5/681* (2013.01); *A61B 5/7267* (2013.01); *A61B 7/006* (2013.01); *G05B 13/0265* (2013.01); *G06F 3/015* (2013.01); *G06K 9/0057* (2013.01); *G06K 9/00536* (2013.01); *G06K 9/00557* (2013.01); *G06K 9/624* (2013.01); *G06K 9/6263* (2013.01)

(58) Field of Classification Search
  USPC .......................................................... 706/12
  See application file for complete search history.

(56) References Cited

U.S. PATENT DOCUMENTS

| | | |
|---|---|---|
| 3,580,243 A | 5/1971 | Johnson |
| 3,620,208 A | 11/1971 | Wayne et al. |
| 3,712,716 A | 1/1973 | Cornsweet et al. |
| 3,735,425 A | 5/1973 | Hoshall et al. |
| 3,880,146 A | 4/1975 | Everett et al. |
| 4,055,168 A | 10/1977 | Miller et al. |
| 4,602,639 A | 7/1986 | Hoogendoorn et al. |
| 4,705,408 A | 11/1987 | Jordi |
| 4,817,064 A | 3/1989 | Milles |
| 4,896,120 A | 1/1990 | Kamil |
| 4,978,213 A | 12/1990 | El Hage |
| 5,003,978 A | 4/1991 | Dunseath, Jr. |
| D322,227 S | 12/1991 | Warhol |
| 5,081,852 A | 1/1992 | Cox |
| 5,103,323 A | 4/1992 | Magarinos et al. |
| 5,231,674 A | 7/1993 | Cleveland et al. |
| 5,251,189 A | 10/1993 | Thorp |
| D348,660 S | 7/1994 | Parsons |
| 5,445,869 A | 8/1995 | Ishikawa et al. |
| 5,462,065 A | 10/1995 | Cusimano |
| 5,467,104 A | 11/1995 | Furness, III et al. |
| 5,482,051 A | 1/1996 | Reddy et al. |
| 5,589,956 A | 12/1996 | Morishima et al. |
| 5,596,339 A | 1/1997 | Furness, III et al. |
| 5,605,059 A | 2/1997 | Woodward |
| 5,625,577 A | 4/1997 | Kunii et al. |
| 5,683,404 A | 11/1997 | Johnson |
| 5,742,421 A | 4/1998 | Wells et al. |
| 6,005,548 A | 12/1999 | Latypov et al. |
| 6,008,781 A | 12/1999 | Furness, III et al. |
| 6,009,210 A | 12/1999 | Kand |
| 6,027,216 A | 2/2000 | Guyton et al. |
| 6,032,530 A | 3/2000 | Hock |
| D422,617 S | 4/2000 | Simioni |
| 6,066,794 A | 5/2000 | Longo |
| 6,184,847 B1 | 2/2001 | Fateh et al. |
| 6,236,476 B1 | 5/2001 | Son et al. |
| 6,238,338 B1 | 5/2001 | DeLuca et al. |
| 6,244,873 B1 | 6/2001 | Hill et al. |
| 6,317,103 B1 | 11/2001 | Furness, III et al. |
| 6,377,277 B1 | 4/2002 | Yamamoto |
| D459,352 S | 6/2002 | Giovanniello |
| 6,411,843 B1 | 6/2002 | Zarychta |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,639,570 B2 | 10/2003 | Furness, III et al. |
| 6,658,287 B1 | 12/2003 | Litt et al. |
| 6,720,984 B1 | 4/2004 | Jorgensen et al. |
| 6,743,982 B2 | 6/2004 | Biegelsen et al. |
| 6,771,294 B1 | 8/2004 | Pulli et al. |
| 6,774,885 B1 | 8/2004 | Even-Zohar |
| 6,807,438 B1 | 10/2004 | Brun Del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,901,286 B1 | 5/2005 | Sinderby et al. |
| 6,927,343 B2 | 8/2005 | Watanabe et al. |
| 6,942,621 B2 | 9/2005 | Avinash et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,028,507 B2 | 4/2006 | Rapport |
| 7,086,218 B1 | 8/2006 | Pasach |
| 7,089,148 B1 | 8/2006 | Bachmann et al. |
| D535,401 S | 1/2007 | Travis et al. |
| 7,173,437 B2 | 2/2007 | Hervieux et al. |
| 7,209,114 B2 | 4/2007 | Radley-Smith |
| D543,212 S | 5/2007 | Marks |
| 7,265,298 B2 | 9/2007 | Maghribi et al. |
| 7,271,774 B2 | 9/2007 | Puuri |
| 7,333,090 B2 | 2/2008 | Tanaka et al. |
| 7,351,975 B2 | 4/2008 | Brady et al. |
| 7,450,107 B2 | 11/2008 | Radley-Smith |
| 7,473,888 B2 | 1/2009 | Wine et al. |
| 7,491,892 B2 | 2/2009 | Wagner et al. |
| 7,517,725 B2 | 4/2009 | Reis |
| 7,558,622 B2 | 7/2009 | Tran |
| 7,574,253 B2 | 8/2009 | Edney et al. |
| 7,580,742 B2 | 8/2009 | Tan et al. |
| 7,596,393 B2 | 9/2009 | Jung et al. |
| 7,618,260 B2 | 11/2009 | Daniel et al. |
| 7,636,549 B2 | 12/2009 | Ma et al. |
| 7,640,007 B2 | 12/2009 | Chen et al. |
| 7,660,126 B2 | 2/2010 | Cho et al. |
| 7,684,105 B2 | 3/2010 | Lamontagne et al. |
| 7,747,113 B2 | 6/2010 | Mukawa et al. |
| 7,761,390 B2 | 7/2010 | Ford |
| 7,773,111 B2 | 8/2010 | Cleveland et al. |
| 7,787,946 B2 | 8/2010 | Stahmann et al. |
| 7,805,386 B2 | 9/2010 | Greer |
| 7,809,435 B1 | 10/2010 | Ettare et al. |
| 7,844,310 B2 | 11/2010 | Anderson |
| D628,616 S | 12/2010 | Yuan |
| 7,850,306 B2 | 12/2010 | Uusitalo et al. |
| 7,870,211 B2 | 1/2011 | Pascal et al. |
| D633,939 S | 3/2011 | Puentes et al. |
| D634,771 S | 3/2011 | Fuchs |
| 7,901,368 B2 | 3/2011 | Flaherty et al. |
| 7,925,100 B2 | 4/2011 | Howell et al. |
| 7,948,763 B2 | 5/2011 | Chuang |
| D640,314 S | 6/2011 | Yang |
| D643,428 S | 8/2011 | Janky et al. |
| D646,192 S | 10/2011 | Woode |
| D649,177 S | 11/2011 | Cho et al. |
| 8,054,061 B2 | 11/2011 | Prance et al. |
| D654,622 S | 2/2012 | Hsu |
| 8,120,828 B2 | 2/2012 | Schwerdtner |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| 8,190,249 B1 | 5/2012 | Gharieb et al. |
| D661,613 S | 6/2012 | Demeglio |
| 8,203,502 B1 | 6/2012 | Chi et al. |
| 8,207,473 B2 | 6/2012 | Axisa et al. |
| 8,212,859 B2 | 7/2012 | Tang et al. |
| D667,482 S | 9/2012 | Healy et al. |
| D669,522 S | 10/2012 | Klinar et al. |
| D669,523 S | 10/2012 | Wakata et al. |
| D671,590 S | 11/2012 | Klinar et al. |
| 8,311,623 B2 | 11/2012 | Sanger |
| 8,348,538 B2 | 1/2013 | Van Loenen et al. |
| 8,351,651 B2 | 1/2013 | Lee |
| 8,355,671 B2 | 1/2013 | Kramer et al. |
| 8,384,683 B2 | 2/2013 | Luo |
| 8,386,025 B2 | 2/2013 | Hoppe |
| 8,389,862 B2 | 3/2013 | Arora et al. |

(56) References Cited

U.S. PATENT DOCUMENTS

| | | |
|---|---|---|
| 8,421,634 B2 | 4/2013 | Tan et al. |
| 8,427,977 B2 | 4/2013 | Workman et al. |
| D682,343 S | 5/2013 | Waters |
| D682,727 S | 5/2013 | Bulgari |
| 8,435,191 B2 | 5/2013 | Barboutis et al. |
| 8,437,844 B2 | 5/2013 | Syed Momen et al. |
| 8,447,704 B2 | 5/2013 | Tan et al. |
| D685,019 S | 6/2013 | Li |
| 8,467,270 B2 | 6/2013 | Gossweiler, III et al. |
| 8,469,741 B2 | 6/2013 | Oster et al. |
| D687,087 S | 7/2013 | Iurilli |
| 8,484,022 B1 | 7/2013 | Vanhoucke |
| D689,862 S | 9/2013 | Liu |
| D692,941 S | 11/2013 | Klinar et al. |
| 8,591,411 B2 | 11/2013 | Banet et al. |
| D695,333 S | 12/2013 | Farnam et al. |
| D695,454 S | 12/2013 | Moore |
| 8,620,361 B2 | 12/2013 | Bailey et al. |
| 8,624,124 B2 | 1/2014 | Koo et al. |
| 8,634,119 B2 | 1/2014 | Bablumyan et al. |
| D701,555 S | 3/2014 | Markovitz et al. |
| 8,666,212 B1 | 3/2014 | Amirparviz |
| 8,702,629 B2 | 4/2014 | Giuffrida et al. |
| 8,704,882 B2 | 4/2014 | Turner |
| D704,248 S | 5/2014 | DiChiara |
| 8,718,980 B2 | 5/2014 | Garudadri et al. |
| 8,743,052 B1 | 6/2014 | Keller et al. |
| 8,744,543 B2 | 6/2014 | Li et al. |
| 8,754,862 B2 | 6/2014 | Zaliva |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,880,163 B2 | 11/2014 | Barachant et al. |
| 8,883,287 B2 | 11/2014 | Boyce et al. |
| 8,890,875 B2 | 11/2014 | Jammes et al. |
| 8,892,479 B2 | 11/2014 | Tan et al. |
| 8,895,865 B2 | 11/2014 | Lenahan et al. |
| D719,568 S | 12/2014 | Heinrich et al. |
| D719,570 S | 12/2014 | Heinrich et al. |
| 8,912,094 B2 | 12/2014 | Koo et al. |
| 8,914,472 B1 | 12/2014 | Lee et al. |
| 8,922,481 B1 | 12/2014 | Kauffmann et al. |
| D723,093 S | 2/2015 | Li |
| 8,954,135 B2 | 2/2015 | Yuen et al. |
| D724,647 S | 3/2015 | Rohrbach |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,037,530 B2 | 5/2015 | Tan et al. |
| 9,086,687 B2 | 7/2015 | Park et al. |
| 9,092,664 B2 | 7/2015 | Forutanpour et al. |
| D736,664 S | 8/2015 | Paradise et al. |
| 9,107,586 B2 | 8/2015 | Tran |
| D738,373 S | 9/2015 | Davies |
| 9,135,708 B2 | 9/2015 | Ebisawa |
| 9,146,730 B2 | 9/2015 | Lazar |
| D741,855 S | 10/2015 | Park et al. |
| 9,170,674 B2 | 10/2015 | Forutanpour et al. |
| D742,272 S | 11/2015 | Bailey et al. |
| D742,874 S | 11/2015 | Cheng et al. |
| D743,963 S | 11/2015 | Osterhout |
| 9,182,826 B2 | 11/2015 | Powledge et al. |
| 9,211,417 B2 | 12/2015 | Heldman et al. |
| 9,218,574 B2 | 12/2015 | Phillipps et al. |
| D747,714 S | 1/2016 | Erbeus |
| D747,759 S | 1/2016 | Ho |
| 9,235,934 B2 | 1/2016 | Mandella et al. |
| 9,240,069 B1 | 1/2016 | Li |
| D750,623 S | 3/2016 | Park et al. |
| D751,065 S | 3/2016 | Magi |
| 9,278,453 B2 | 3/2016 | Assad |
| 9,299,248 B2 | 3/2016 | Lake et al. |
| D756,359 S | 5/2016 | Bailey et al. |
| 9,329,694 B2 | 5/2016 | Slonneger |
| 9,341,659 B2 | 5/2016 | Poupyrev et al. |
| 9,349,280 B2 | 5/2016 | Baldwin et al. |
| 9,351,653 B1 | 5/2016 | Harrison |
| D758,476 S | 6/2016 | Ho |
| D760,313 S | 6/2016 | Ho et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,402,582 B1 | 8/2016 | Parviz et al. |
| 9,408,316 B2 | 8/2016 | Bailey et al. |
| 9,418,927 B2 | 8/2016 | Axisa et al. |
| D766,895 S | 9/2016 | Choi |
| 9,439,566 B2 | 9/2016 | Arne et al. |
| D768,627 S | 10/2016 | Rochat et al. |
| 9,459,697 B2 | 10/2016 | Bedikian et al. |
| 9,472,956 B2 | 10/2016 | Michaelis et al. |
| 9,477,313 B2 | 10/2016 | Mistry et al. |
| D771,735 S | 11/2016 | Lee et al. |
| 9,483,123 B2 | 11/2016 | Aleem et al. |
| 9,529,434 B2 | 12/2016 | Choi et al. |
| D780,828 S | 3/2017 | Bonaventura et al. |
| D780,829 S | 3/2017 | Bonaventura et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,652,047 B2 | 5/2017 | Mullins et al. |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,807,221 B2 | 10/2017 | Bailey et al. |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 9,921,641 B1 | 3/2018 | Worley, III et al. |
| 9,996,983 B2 | 6/2018 | Mullins |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,185,416 B2 | 1/2019 | Mistry et al. |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,429,928 B2 | 10/2019 | Morun et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,520,378 B1 | 12/2019 | Brown et al. |
| 10,528,135 B2 | 1/2020 | Bailey et al. |
| 10,558,273 B2 | 2/2020 | Park et al. |
| 10,592,001 B2 | 3/2020 | Berenzweig et al. |
| 10,610,737 B1 | 4/2020 | Crawford |
| 10,676,083 B1 | 6/2020 | De Sapio et al. |
| 10,687,759 B2 | 6/2020 | Guo et al. |
| 10,905,350 B2 | 2/2021 | Berenzweig et al. |
| 10,905,383 B2 | 2/2021 | Barachant |
| 10,937,414 B2 | 3/2021 | Berenzweig et al. |
| 10,990,174 B2 | 4/2021 | Kaifosh et al. |
| 11,009,951 B2 | 5/2021 | Bailey et al. |
| 11,150,730 B1 | 10/2021 | Anderson et al. |
| 2001/0033402 A1 | 10/2001 | Popovich |

(56) References Cited

U.S. PATENT DOCUMENTS

| | | |
|---|---|---|
| 2002/0003627 A1 | 1/2002 | Rieder |
| 2002/0009972 A1 | 1/2002 | Amento et al. |
| 2002/0030636 A1 | 3/2002 | Richards |
| 2002/0032386 A1 | 3/2002 | Sackner et al. |
| 2002/0077534 A1 | 6/2002 | DuRousseau |
| 2002/0094701 A1 | 7/2002 | Biegelsen et al. |
| 2002/0120415 A1 | 8/2002 | Millott et al. |
| 2002/0120916 A1 | 8/2002 | Snider, Jr. |
| 2002/0198472 A1 | 12/2002 | Kramer |
| 2003/0030595 A1 | 2/2003 | Radley-Smith |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2003/0144829 A1 | 7/2003 | Geatz et al. |
| 2003/0171921 A1 | 9/2003 | Manabe et al. |
| 2003/0182630 A1 | 9/2003 | Saund |
| 2003/0184544 A1 | 10/2003 | Prudent |
| 2004/0010210 A1 | 1/2004 | Avinash et al. |
| 2004/0024312 A1 | 2/2004 | Zheng |
| 2004/0054273 A1 | 3/2004 | Finneran et al. |
| 2004/0068409 A1 | 4/2004 | Tanaka et al. |
| 2004/0073104 A1 | 4/2004 | Brun Del Re et al. |
| 2004/0080499 A1 | 4/2004 | Lui |
| 2004/0092839 A1 | 5/2004 | Shin et al. |
| 2004/0194500 A1 | 10/2004 | Rapport |
| 2004/0210165 A1 | 10/2004 | Marmaropoulos et al. |
| 2004/0243342 A1 | 12/2004 | Rekimoto |
| 2004/0254617 A1 | 12/2004 | Hemmerling et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0070791 A1 | 3/2005 | Edney et al. |
| 2005/0115561 A1 | 6/2005 | Stahmann et al. |
| 2005/0119701 A1 | 6/2005 | Lauter et al. |
| 2005/0177038 A1 | 8/2005 | Kolpin et al. |
| 2005/0179644 A1 | 8/2005 | Alsio et al. |
| 2006/0018833 A1 | 1/2006 | Murphy et al. |
| 2006/0037359 A1 | 2/2006 | Stinespring |
| 2006/0058699 A1 | 3/2006 | Vitiello et al. |
| 2006/0061544 A1 | 3/2006 | Min et al. |
| 2006/0121958 A1 | 6/2006 | Jung et al. |
| 2006/0129057 A1 | 6/2006 | Maekawa et al. |
| 2006/0132705 A1 | 6/2006 | Li |
| 2006/0149338 A1 | 7/2006 | Flaherty et al. |
| 2006/0211956 A1 | 9/2006 | Sankai |
| 2006/0238707 A1 | 10/2006 | Elvesjo et al. |
| 2007/0009151 A1 | 1/2007 | Pittman et al. |
| 2007/0016265 A1 | 1/2007 | Davoodi et al. |
| 2007/0023662 A1 | 2/2007 | Brady et al. |
| 2007/0078308 A1 | 4/2007 | Daly |
| 2007/0132785 A1 | 6/2007 | Ebersole, Jr. et al. |
| 2007/0148624 A1 | 6/2007 | Nativ |
| 2007/0172797 A1 | 7/2007 | Hada et al. |
| 2007/0177770 A1 | 8/2007 | Derchak et al. |
| 2007/0185697 A1 | 8/2007 | Tan et al. |
| 2007/0256494 A1 | 11/2007 | Nakamura et al. |
| 2007/0276270 A1 | 11/2007 | Tran |
| 2007/0279852 A1 | 12/2007 | Daniel et al. |
| 2007/0285399 A1 | 12/2007 | Lund |
| 2008/0001735 A1 | 1/2008 | Tran |
| 2008/0032638 A1 | 2/2008 | Anderson |
| 2008/0051673 A1 | 2/2008 | Kong et al. |
| 2008/0052643 A1 | 2/2008 | Ike et al. |
| 2008/0058668 A1 | 3/2008 | Seyed Momen et al. |
| 2008/0103639 A1 | 5/2008 | Troy et al. |
| 2008/0103769 A1 | 5/2008 | Schultz et al. |
| 2008/0136775 A1 | 6/2008 | Conant |
| 2008/0152217 A1 | 6/2008 | Greer |
| 2008/0163130 A1 | 7/2008 | Westerman |
| 2008/0214360 A1 | 9/2008 | Stirling et al. |
| 2008/0221487 A1 | 9/2008 | Zohar et al. |
| 2008/0262772 A1 | 10/2008 | Luinge et al. |
| 2008/0278497 A1 | 11/2008 | Jammes et al. |
| 2008/0285805 A1 | 11/2008 | Luinge et al. |
| 2009/0005700 A1 | 1/2009 | Joshi et al. |
| 2009/0007597 A1 | 1/2009 | Hanevold |
| 2009/0027337 A1 | 1/2009 | Hildreth |
| 2009/0031757 A1 | 2/2009 | Harding |
| 2009/0040016 A1 | 2/2009 | Ikeda |
| 2009/0051544 A1 | 2/2009 | Niknejad |
| 2009/0079607 A1 | 3/2009 | Denison et al. |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0085864 A1 | 4/2009 | Kutliroff et al. |
| 2009/0102580 A1 | 4/2009 | Uchaykin |
| 2009/0109241 A1 | 4/2009 | Tsujimoto |
| 2009/0112080 A1 | 4/2009 | Matthews |
| 2009/0124881 A1 | 5/2009 | Rytky |
| 2009/0147004 A1 | 6/2009 | Ramon et al. |
| 2009/0179824 A1 | 7/2009 | Tsujimoto et al. |
| 2009/0189864 A1 | 7/2009 | Walker et al. |
| 2009/0189867 A1 | 7/2009 | Krah et al. |
| 2009/0195497 A1 | 8/2009 | Fitzgerald et al. |
| 2009/0204031 A1 | 8/2009 | McNames et al. |
| 2009/0207464 A1 | 8/2009 | Wiltshire et al. |
| 2009/0209878 A1 | 8/2009 | Sanger |
| 2009/0251407 A1 | 10/2009 | Flake et al. |
| 2009/0258669 A1 | 10/2009 | Nie et al. |
| 2009/0265671 A1 | 10/2009 | Sachs et al. |
| 2009/0318785 A1 | 12/2009 | Ishikawa et al. |
| 2009/0319230 A1 | 12/2009 | Case, Jr. et al. |
| 2009/0322653 A1 | 12/2009 | Putilin et al. |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0041974 A1 | 2/2010 | Ting et al. |
| 2010/0063794 A1 | 3/2010 | Hernandez-Rebollar |
| 2010/0066664 A1 | 3/2010 | Son et al. |
| 2010/0106044 A1 | 4/2010 | Linderman |
| 2010/0113910 A1 | 5/2010 | Brauers et al. |
| 2010/0142015 A1 | 6/2010 | Kuwahara et al. |
| 2010/0149073 A1 | 6/2010 | Chaum et al. |
| 2010/0150415 A1 | 6/2010 | Atkinson et al. |
| 2010/0228487 A1 | 9/2010 | Leuthardt et al. |
| 2010/0234696 A1 | 9/2010 | Li et al. |
| 2010/0240981 A1 | 9/2010 | Barboutis et al. |
| 2010/0249635 A1 | 9/2010 | Van Der Reijden |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0306713 A1 | 12/2010 | Geisner et al. |
| 2010/0315266 A1 | 12/2010 | Gunawardana et al. |
| 2010/0317958 A1 | 12/2010 | Beck et al. |
| 2011/0007035 A1 | 1/2011 | Shai |
| 2011/0018754 A1 | 1/2011 | Tojima et al. |
| 2011/0025982 A1 | 2/2011 | Takahashi |
| 2011/0054360 A1 | 3/2011 | Son et al. |
| 2011/0065319 A1 | 3/2011 | Oster et al. |
| 2011/0066381 A1 | 3/2011 | Garudadri et al. |
| 2011/0072510 A1 | 3/2011 | Cheswick |
| 2011/0077484 A1 | 3/2011 | Van Slyke et al. |
| 2011/0082838 A1 | 4/2011 | Niemela |
| 2011/0092826 A1 | 4/2011 | Lee et al. |
| 2011/0119216 A1 | 5/2011 | Wigdor |
| 2011/0133934 A1 | 6/2011 | Tan et al. |
| 2011/0134026 A1 | 6/2011 | Kang et al. |
| 2011/0151974 A1 | 6/2011 | Deaguero |
| 2011/0166434 A1 | 7/2011 | Gargiulo |
| 2011/0172503 A1 | 7/2011 | Knepper et al. |
| 2011/0173204 A1 | 7/2011 | Murillo et al. |
| 2011/0173574 A1 | 7/2011 | Clavin et al. |
| 2011/0181527 A1 | 7/2011 | Capela et al. |
| 2011/0205242 A1 | 8/2011 | Friesen |
| 2011/0213278 A1 | 9/2011 | Horak et al. |
| 2011/0221672 A1 | 9/2011 | Osterhout et al. |
| 2011/0224507 A1 | 9/2011 | Banet et al. |
| 2011/0224556 A1 | 9/2011 | Moon et al. |
| 2011/0224564 A1 | 9/2011 | Moon et al. |
| 2011/0230782 A1 | 9/2011 | Bartol et al. |
| 2011/0248914 A1 | 10/2011 | Sherr |
| 2011/0262002 A1 | 10/2011 | Lee |

(56) References Cited

U.S. PATENT DOCUMENTS

| | | |
|---|---|---|
| 2011/0270135 A1 | 11/2011 | Dooley et al. |
| 2011/0295100 A1 | 12/2011 | Hegde et al. |
| 2011/0313762 A1 | 12/2011 | Ben-David et al. |
| 2012/0002256 A1 | 1/2012 | Lacoste et al. |
| 2012/0007821 A1 | 1/2012 | Zaliva |
| 2012/0029322 A1 | 2/2012 | Wartena et al. |
| 2012/0051005 A1 | 3/2012 | Vanfleteren et al. |
| 2012/0052268 A1 | 3/2012 | Axisa et al. |
| 2012/0053439 A1 | 3/2012 | Ylostalo et al. |
| 2012/0066163 A1 | 3/2012 | Balls et al. |
| 2012/0071092 A1 | 3/2012 | Pasquero et al. |
| 2012/0071780 A1 | 3/2012 | Barachant et al. |
| 2012/0101357 A1 | 4/2012 | Hoskuldsson et al. |
| 2012/0117514 A1 | 5/2012 | Kim et al. |
| 2012/0139817 A1 | 6/2012 | Freeman |
| 2012/0157789 A1 | 6/2012 | Kangas et al. |
| 2012/0157886 A1 | 6/2012 | Tenn |
| 2012/0165695 A1 | 6/2012 | Kidmose et al. |
| 2012/0182309 A1 | 7/2012 | Griffin et al. |
| 2012/0184838 A1 | 7/2012 | John |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0226130 A1 | 9/2012 | De Graff et al. |
| 2012/0249797 A1 | 10/2012 | Haddick et al. |
| 2012/0265090 A1 | 10/2012 | Fink et al. |
| 2012/0265480 A1 | 10/2012 | Oshima |
| 2012/0275621 A1 | 11/2012 | Elko |
| 2012/0283526 A1 | 11/2012 | Gommesen et al. |
| 2012/0283896 A1 | 11/2012 | Persaud et al. |
| 2012/0293548 A1 | 11/2012 | Perez et al. |
| 2012/0302858 A1 | 11/2012 | Kidmose et al. |
| 2012/0320532 A1 | 12/2012 | Wang |
| 2012/0323521 A1 | 12/2012 | De Foras et al. |
| 2013/0004033 A1 | 1/2013 | Trugenberger |
| 2013/0005303 A1 | 1/2013 | Song et al. |
| 2013/0016292 A1 | 1/2013 | Miao et al. |
| 2013/0016413 A1 | 1/2013 | Saeedi et al. |
| 2013/0020948 A1 | 1/2013 | Han et al. |
| 2013/0027341 A1 | 1/2013 | Mastandrea |
| 2013/0038707 A1 | 2/2013 | Cunningham et al. |
| 2013/0077820 A1 | 3/2013 | Marais et al. |
| 2013/0080794 A1 | 3/2013 | Hsieh |
| 2013/0106686 A1 | 5/2013 | Bennett |
| 2013/0123656 A1 | 5/2013 | Heck |
| 2013/0123666 A1 | 5/2013 | Giuffrida et al. |
| 2013/0127708 A1 | 5/2013 | Jung et al. |
| 2013/0131538 A1 | 5/2013 | Gaw et al. |
| 2013/0135223 A1 | 5/2013 | Shai |
| 2013/0135722 A1 | 5/2013 | Yokoyama |
| 2013/0141375 A1 | 6/2013 | Ludwig et al. |
| 2013/0144629 A1 | 6/2013 | Johnston et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0207889 A1 | 8/2013 | Chang et al. |
| 2013/0215235 A1 | 8/2013 | Russell |
| 2013/0217998 A1 | 8/2013 | Mahfouz et al. |
| 2013/0221996 A1 | 8/2013 | Poupyrev et al. |
| 2013/0222384 A1 | 8/2013 | Futterer |
| 2013/0232095 A1 | 9/2013 | Tan et al. |
| 2013/0259238 A1 | 10/2013 | Xiang et al. |
| 2013/0265229 A1 | 10/2013 | Forutanpour et al. |
| 2013/0265437 A1 | 10/2013 | Thorn et al. |
| 2013/0271292 A1 | 10/2013 | McDermott |
| 2013/0285901 A1 | 10/2013 | Lee et al. |
| 2013/0285913 A1 | 10/2013 | Griffin et al. |
| 2013/0293580 A1 | 11/2013 | Spivack |
| 2013/0310979 A1 | 11/2013 | Herr et al. |
| 2013/0312256 A1 | 11/2013 | Wesselmann et al. |
| 2013/0317382 A1 | 11/2013 | Le |
| 2013/0317648 A1 | 11/2013 | Assad |
| 2013/0332196 A1 | 12/2013 | Pinsker |
| 2013/0335302 A1 | 12/2013 | Crane et al. |
| 2014/0005743 A1 | 1/2014 | Giuffrida et al. |
| 2014/0020945 A1 | 1/2014 | Hurwitz et al. |
| 2014/0028539 A1 | 1/2014 | Newham et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0051946 A1 | 2/2014 | Arne et al. |
| 2014/0052150 A1 | 2/2014 | Taylor et al. |
| 2014/0074179 A1 | 3/2014 | Heldman et al. |
| 2014/0092009 A1 | 4/2014 | Yen et al. |
| 2014/0094675 A1 | 4/2014 | Luna et al. |
| 2014/0098018 A1 | 4/2014 | Kim et al. |
| 2014/0100432 A1 | 4/2014 | Golda et al. |
| 2014/0107493 A1 | 4/2014 | Yuen et al. |
| 2014/0121471 A1 | 5/2014 | Walker |
| 2014/0122958 A1 | 5/2014 | Greenebrg et al. |
| 2014/0132512 A1 | 5/2014 | Gomez Sainz-Garcia |
| 2014/0139422 A1 | 5/2014 | Mistry et al. |
| 2014/0142937 A1 | 5/2014 | Powledge et al. |
| 2014/0143064 A1 | 5/2014 | Tran |
| 2014/0147820 A1 | 5/2014 | Snow et al. |
| 2014/0157168 A1 | 6/2014 | Albouyeh et al. |
| 2014/0194062 A1 | 7/2014 | Palin et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0200432 A1 | 7/2014 | Banerji et al. |
| 2014/0201666 A1 | 7/2014 | Bedikian et al. |
| 2014/0202643 A1 | 7/2014 | Hikmet et al. |
| 2014/0204455 A1 | 7/2014 | Popovich et al. |
| 2014/0223462 A1 | 8/2014 | Aimone et al. |
| 2014/0226193 A1 | 8/2014 | Sun |
| 2014/0232651 A1 | 8/2014 | Kress et al. |
| 2014/0236031 A1 | 8/2014 | Banet et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0257141 A1 | 9/2014 | Giuffrida et al. |
| 2014/0258864 A1 | 9/2014 | Shenoy et al. |
| 2014/0277622 A1 | 9/2014 | Raniere |
| 2014/0278139 A1 | 9/2014 | Hong et al. |
| 2014/0278441 A1 | 9/2014 | Ton et al. |
| 2014/0279860 A1 | 9/2014 | Pan et al. |
| 2014/0282282 A1 | 9/2014 | Holz |
| 2014/0285326 A1 | 9/2014 | Luna et al. |
| 2014/0285429 A1 | 9/2014 | Simmons |
| 2014/0297528 A1 | 10/2014 | Agrawal et al. |
| 2014/0299362 A1 | 10/2014 | Park et al. |
| 2014/0304665 A1 | 10/2014 | Holz |
| 2014/0310595 A1 | 10/2014 | Acharya et al. |
| 2014/0330404 A1 | 11/2014 | Abdelghani et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hsu et al. |
| 2014/0344731 A1 | 11/2014 | Holz |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0355825 A1 | 12/2014 | Kim et al. |
| 2014/0358024 A1 | 12/2014 | Nelson et al. |
| 2014/0358825 A1 | 12/2014 | Phillipps et al. |
| 2014/0359540 A1 | 12/2014 | Kelsey et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0368424 A1 | 12/2014 | Choi et al. |
| 2014/0368428 A1 | 12/2014 | Pinault |
| 2014/0368474 A1 | 12/2014 | Kim et al. |
| 2014/0368896 A1 | 12/2014 | Nakazono et al. |
| 2014/0375465 A1 | 12/2014 | Fenuccio et al. |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0011857 A1 | 1/2015 | Henson et al. |
| 2015/0019135 A1 | 1/2015 | Kacyvenski et al. |
| 2015/0025355 A1 | 1/2015 | Bailey et al. |
| 2015/0029092 A1 | 1/2015 | Holz et al. |

(56) References Cited

U.S. PATENT DOCUMENTS

| | | |
|---|---|---|
| 2015/0035827 A1 | 2/2015 | Yamaoka et al. |
| 2015/0036221 A1 | 2/2015 | Stephenson |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0065840 A1 | 3/2015 | Bailey |
| 2015/0070270 A1 | 3/2015 | Bailey et al. |
| 2015/0070274 A1 | 3/2015 | Morozov |
| 2015/0072326 A1 | 3/2015 | Mauri et al. |
| 2015/0084860 A1 | 3/2015 | Aleem et al. |
| 2015/0091790 A1 | 4/2015 | Forutanpour et al. |
| 2015/0094564 A1 | 4/2015 | Tashman et al. |
| 2015/0099946 A1 | 4/2015 | Sahin |
| 2015/0106052 A1 | 4/2015 | Balakrishnan et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0148728 A1 | 5/2015 | Sallum et al. |
| 2015/0157944 A1 | 6/2015 | Gottlieb |
| 2015/0160621 A1 | 6/2015 | Yilmaz |
| 2015/0169074 A1 | 6/2015 | Ataee et al. |
| 2015/0170421 A1 | 6/2015 | Mandella et al. |
| 2015/0177841 A1 | 6/2015 | Vanblon et al. |
| 2015/0182113 A1 | 7/2015 | Utter, II |
| 2015/0182130 A1 | 7/2015 | Utter, II |
| 2015/0182160 A1 | 7/2015 | Kim et al. |
| 2015/0182163 A1 | 7/2015 | Utter |
| 2015/0182164 A1 | 7/2015 | Utter, II |
| 2015/0182165 A1 | 7/2015 | Miller et al. |
| 2015/0185838 A1 | 7/2015 | Camacho-Perez et al. |
| 2015/0186609 A1 | 7/2015 | Utter, II |
| 2015/0187355 A1 | 7/2015 | Parkinson et al. |
| 2015/0193949 A1 | 7/2015 | Katz et al. |
| 2015/0199025 A1 | 7/2015 | Holz |
| 2015/0205126 A1 | 7/2015 | Schowengerdt |
| 2015/0205134 A1 | 7/2015 | Bailey et al. |
| 2015/0213191 A1 | 7/2015 | Abdelghani et al. |
| 2015/0216475 A1 | 8/2015 | Luna et al. |
| 2015/0220152 A1 | 8/2015 | Tait et al. |
| 2015/0223716 A1 | 8/2015 | Korkala et al. |
| 2015/0230756 A1 | 8/2015 | Luna et al. |
| 2015/0234426 A1 | 8/2015 | Bailey et al. |
| 2015/0237716 A1 | 8/2015 | Su et al. |
| 2015/0242009 A1 | 8/2015 | Xiao et al. |
| 2015/0242120 A1 | 8/2015 | Rodriguez |
| 2015/0242575 A1 | 8/2015 | Abovitz et al. |
| 2015/0261306 A1 | 9/2015 | Lake |
| 2015/0261318 A1 | 9/2015 | Scavezze et al. |
| 2015/0272483 A1 | 10/2015 | Etemad et al. |
| 2015/0277575 A1 | 10/2015 | Ataee et al. |
| 2015/0288944 A1 | 10/2015 | Nistico et al. |
| 2015/0289995 A1 | 10/2015 | Wilkinson et al. |
| 2015/0296553 A1 | 10/2015 | DiFranco et al. |
| 2015/0302168 A1 | 10/2015 | De Sapio et al. |
| 2015/0305672 A1 | 10/2015 | Grey et al. |
| 2015/0309563 A1 | 10/2015 | Connor |
| 2015/0309582 A1 | 10/2015 | Gupta |
| 2015/0310766 A1 | 10/2015 | Alshehri et al. |
| 2015/0312175 A1 | 10/2015 | Langholz |
| 2015/0313496 A1 | 11/2015 | Connor |
| 2015/0323998 A1 | 11/2015 | Kudekar et al. |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0351690 A1 | 12/2015 | Toth et al. |
| 2015/0355716 A1 | 12/2015 | Balasubramanian et al. |
| 2015/0355718 A1 | 12/2015 | Slonneger |
| 2015/0362734 A1 | 12/2015 | Moser et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2015/0378161 A1 | 12/2015 | Bailey et al. |
| 2015/0378162 A1 | 12/2015 | Bailey et al. |
| 2015/0378164 A1 | 12/2015 | Bailey et al. |
| 2015/0379770 A1 | 12/2015 | Haley, Jr. et al. |
| 2016/0011668 A1 | 1/2016 | Gilad-Bachrach et al. |
| 2016/0020500 A1 | 1/2016 | Matsuda |
| 2016/0026853 A1 | 1/2016 | Wexler et al. |
| 2016/0033771 A1 | 2/2016 | Tremblay et al. |
| 2016/0049073 A1 | 2/2016 | Lee |
| 2016/0050037 A1 | 2/2016 | Webb |
| 2016/0071319 A1 | 3/2016 | Fallon et al. |
| 2016/0092504 A1 | 3/2016 | Mitri et al. |
| 2016/0099010 A1 | 4/2016 | Sainath et al. |
| 2016/0107309 A1 | 4/2016 | Walsh et al. |
| 2016/0113587 A1 | 4/2016 | Kothe et al. |
| 2016/0144172 A1 | 5/2016 | Hsueh et al. |
| 2016/0150636 A1 | 5/2016 | Otsubo |
| 2016/0156762 A1 | 6/2016 | Bailey et al. |
| 2016/0162604 A1 | 6/2016 | Xiaoli et al. |
| 2016/0170710 A1 | 6/2016 | Kim et al. |
| 2016/0187992 A1 | 6/2016 | Yamamoto et al. |
| 2016/0195928 A1 | 7/2016 | Wagner et al. |
| 2016/0199699 A1 | 7/2016 | Klassen |
| 2016/0202081 A1 | 7/2016 | Debieuvre et al. |
| 2016/0206206 A1 | 7/2016 | Avila et al. |
| 2016/0207201 A1 | 7/2016 | Herr et al. |
| 2016/0217614 A1 | 7/2016 | Kraver et al. |
| 2016/0235323 A1 | 8/2016 | Tadi et al. |
| 2016/0238845 A1 | 8/2016 | Alexander et al. |
| 2016/0239080 A1 | 8/2016 | Marcolina et al. |
| 2016/0242646 A1 | 8/2016 | Obma |
| 2016/0259407 A1 | 9/2016 | Schick |
| 2016/0262687 A1 | 9/2016 | Imperial |
| 2016/0263458 A1 | 9/2016 | Mather et al. |
| 2016/0274365 A1 | 9/2016 | Bailey et al. |
| 2016/0274732 A1 | 9/2016 | Bang et al. |
| 2016/0274758 A1 | 9/2016 | Bailey |
| 2016/0282947 A1 | 9/2016 | Schwarz et al. |
| 2016/0291768 A1 | 10/2016 | Cho et al. |
| 2016/0292497 A1 | 10/2016 | Kehtarnavaz et al. |
| 2016/0309249 A1 | 10/2016 | Wu et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0314623 A1 | 10/2016 | Coleman et al. |
| 2016/0327796 A1 | 11/2016 | Bailey et al. |
| 2016/0327797 A1 | 11/2016 | Bailey et al. |
| 2016/0342227 A1 | 11/2016 | Natzke et al. |
| 2016/0349514 A1 | 12/2016 | Alexander et al. |
| 2016/0349515 A1 | 12/2016 | Alexander et al. |
| 2016/0349516 A1 | 12/2016 | Alexander et al. |
| 2016/0350973 A1 | 12/2016 | Shapira et al. |
| 2016/0377865 A1 | 12/2016 | Alexander et al. |
| 2016/0377866 A1 | 12/2016 | Alexander et al. |
| 2017/0025026 A1 | 1/2017 | Ortiz Catalan |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068095 A1 | 3/2017 | Holland et al. |
| 2017/0068445 A1 | 3/2017 | Lee et al. |
| 2017/0075426 A1 | 3/2017 | Camacho Perez et al. |
| 2017/0079828 A1 | 3/2017 | Pedtke et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0095178 A1 | 4/2017 | Schoen et al. |
| 2017/0097753 A1 | 4/2017 | Bailey et al. |
| 2017/0115483 A1 | 4/2017 | Aleem et al. |
| 2017/0119472 A1 | 5/2017 | Herrmann et al. |
| 2017/0123487 A1 | 5/2017 | Hazra et al. |
| 2017/0124474 A1 | 5/2017 | Kashyap |
| 2017/0124816 A1 | 5/2017 | Yang et al. |
| 2017/0127354 A1 | 5/2017 | Garland et al. |
| 2017/0147077 A1 | 5/2017 | Park et al. |
| 2017/0153701 A1 | 6/2017 | Mahon et al. |
| 2017/0161635 A1 | 6/2017 | Oono et al. |
| 2017/0188878 A1 | 7/2017 | Lee |
| 2017/0188980 A1 | 7/2017 | Ash |

(56) References Cited

U.S. PATENT DOCUMENTS

| | | |
|---|---|---|
| 2017/0197142 A1 | 7/2017 | Stafford et al. |
| 2017/0205876 A1 | 7/2017 | Vidal et al. |
| 2017/0209055 A1 | 7/2017 | Pantelopoulos et al. |
| 2017/0212290 A1 | 7/2017 | Alexander et al. |
| 2017/0212349 A1 | 7/2017 | Bailey et al. |
| 2017/0219829 A1 | 8/2017 | Bailey |
| 2017/0220923 A1 | 8/2017 | Bae et al. |
| 2017/0237789 A1 | 8/2017 | Harner et al. |
| 2017/0237901 A1 | 8/2017 | Lee et al. |
| 2017/0259167 A1 | 9/2017 | Cook et al. |
| 2017/0262064 A1 | 9/2017 | Ofir et al. |
| 2017/0277282 A1 | 9/2017 | Go |
| 2017/0285744 A1 | 10/2017 | Juliato |
| 2017/0285756 A1 | 10/2017 | Wang et al. |
| 2017/0285757 A1 | 10/2017 | Robertson et al. |
| 2017/0285848 A1 | 10/2017 | Rosenberg et al. |
| 2017/0296363 A1 | 10/2017 | Yetkin et al. |
| 2017/0299956 A1 | 10/2017 | Holland et al. |
| 2017/0301630 A1 | 10/2017 | Nguyen et al. |
| 2017/0308118 A1 | 10/2017 | Ito |
| 2017/0312614 A1 | 11/2017 | Tran et al. |
| 2017/0329392 A1 | 11/2017 | Keskin et al. |
| 2017/0329404 A1 | 11/2017 | Keskin et al. |
| 2017/0340506 A1 | 11/2017 | Zhang et al. |
| 2017/0344706 A1 | 11/2017 | Torres et al. |
| 2017/0347908 A1 | 12/2017 | Watanabe et al. |
| 2017/0371403 A1 | 12/2017 | Wetzler et al. |
| 2018/0000367 A1 | 1/2018 | Longinotti-Buitoni |
| 2018/0018825 A1 | 1/2018 | Kim et al. |
| 2018/0020285 A1 | 1/2018 | Zass |
| 2018/0020951 A1 | 1/2018 | Kaifosh et al. |
| 2018/0020978 A1 | 1/2018 | Kaifosh et al. |
| 2018/0020990 A1 | 1/2018 | Park et al. |
| 2018/0024634 A1 | 1/2018 | Kaifosh et al. |
| 2018/0024635 A1 | 1/2018 | Kaifosh et al. |
| 2018/0024641 A1 | 1/2018 | Mao et al. |
| 2018/0064363 A1 | 3/2018 | Morun et al. |
| 2018/0067553 A1 | 3/2018 | Morun et al. |
| 2018/0068489 A1 | 3/2018 | Kim et al. |
| 2018/0074332 A1 | 3/2018 | Li et al. |
| 2018/0081439 A1 | 3/2018 | Daniels |
| 2018/0088675 A1 | 3/2018 | Vogel et al. |
| 2018/0088765 A1 | 3/2018 | Bailey |
| 2018/0092599 A1 | 4/2018 | Kerth et al. |
| 2018/0093181 A1 | 4/2018 | Goslin et al. |
| 2018/0095542 A1 | 4/2018 | Mallinson |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0107275 A1 | 4/2018 | Chen et al. |
| 2018/0120948 A1 | 5/2018 | Aleem et al. |
| 2018/0133551 A1 | 5/2018 | Chang et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0168905 A1 | 6/2018 | Goodall et al. |
| 2018/0178008 A1 | 6/2018 | Bouton et al. |
| 2018/0217249 A1 | 8/2018 | La Salla et al. |
| 2018/0239430 A1 | 8/2018 | Tadi et al. |
| 2018/0240459 A1 | 8/2018 | Weng et al. |
| 2018/0247443 A1 | 8/2018 | Briggs et al. |
| 2018/0279919 A1 | 10/2018 | Bansbach et al. |
| 2018/0301057 A1 | 10/2018 | Hargrove et al. |
| 2018/0307314 A1 | 10/2018 | Connor |
| 2018/0314879 A1 | 11/2018 | Khwaja et al. |
| 2018/0321745 A1 | 11/2018 | Morun et al. |
| 2018/0321746 A1 | 11/2018 | Morun et al. |
| 2018/0330549 A1 | 11/2018 | Brenton |
| 2018/0333575 A1 | 11/2018 | Bouton |
| 2018/0344195 A1 | 12/2018 | Morun et al. |
| 2018/0356890 A1 | 12/2018 | Zhang et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0027141 A1 | 1/2019 | Strong et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0056422 A1 | 2/2019 | Park et al. |
| 2019/0076716 A1 | 3/2019 | Chiou et al. |
| 2019/0089898 A1 | 3/2019 | Kim et al. |
| 2019/0113973 A1 | 4/2019 | Coleman et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0196585 A1 | 6/2019 | Laszlo et al. |
| 2019/0196586 A1 | 6/2019 | Laszlo et al. |
| 2019/0197778 A1 | 6/2019 | Sachdeva et al. |
| 2019/0209034 A1 | 7/2019 | Deno et al. |
| 2019/0212817 A1 | 7/2019 | Kaifosh et al. |
| 2019/0216619 A1 | 7/2019 | McDonnall et al. |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0279407 A1 | 9/2019 | McHugh et al. |
| 2019/0294243 A1 | 9/2019 | Laszlo et al. |
| 2019/0324549 A1 | 10/2019 | Araki et al. |
| 2019/0332140 A1 | 10/2019 | Wang et al. |
| 2019/0348026 A1 | 11/2019 | Berenzweig et al. |
| 2019/0348027 A1 | 11/2019 | Berenzweig et al. |
| 2019/0357787 A1 | 11/2019 | Barachant et al. |
| 2019/0362557 A1 | 11/2019 | Lacey et al. |
| 2020/0042089 A1 | 2/2020 | Ang et al. |
| 2020/0057661 A1 | 2/2020 | Bendfeldt |
| 2020/0065569 A1 | 2/2020 | Nduka et al. |
| 2020/0069210 A1 | 3/2020 | Berenzweig et al. |
| 2020/0069211 A1 | 3/2020 | Berenzweig et al. |
| 2020/0073483 A1 | 3/2020 | Berenzweig et al. |
| 2020/0077955 A1 | 3/2020 | Shui et al. |
| 2020/0097081 A1 | 3/2020 | Stone et al. |
| 2020/0097083 A1 | 3/2020 | Mao et al. |
| 2020/0111260 A1 | 4/2020 | Osborn et al. |
| 2020/0125171 A1 | 4/2020 | Morun et al. |
| 2020/0142490 A1 | 5/2020 | Xiong et al. |
| 2020/0143795 A1 | 5/2020 | Park et al. |
| 2020/0159322 A1 | 5/2020 | Morun et al. |
| 2020/0163562 A1 | 5/2020 | Neaves |
| 2020/0205932 A1 | 7/2020 | Zar et al. |
| 2020/0225320 A1 | 7/2020 | Belskikh et al. |
| 2020/0245873 A1 | 8/2020 | Frank et al. |
| 2020/0249752 A1 | 8/2020 | Parshionikar |
| 2020/0275895 A1 | 9/2020 | Barachant |
| 2020/0301509 A1 | 9/2020 | Liu et al. |
| 2020/0305795 A1 | 10/2020 | Floyd et al. |
| 2020/0320335 A1 | 10/2020 | Shamun et al. |
| 2021/0109598 A1 | 4/2021 | Zhang et al. |
| 2021/0117523 A1 | 4/2021 | Kim et al. |
| 2021/0290159 A1 | 9/2021 | Bruinsma et al. |
| 2022/0256706 A1 | 8/2022 | Xiong et al. |

FOREIGN PATENT DOCUMENTS

| | | |
|---|---|---|
| CA | 2939644 A1 | 8/2015 |
| CN | 1838933 A | 9/2006 |
| CN | 102246125 A | 11/2011 |
| CN | 103777752 A | 5/2014 |
| CN | 105009031 A | 10/2015 |
| CN | 105190477 A | 12/2015 |
| CN | 105190578 A | 12/2015 |
| CN | 106102504 A | 11/2016 |
| CN | 110300542 A | 10/2019 |
| CN | 111902077 A | 11/2020 |
| CN | 112074225 A | 12/2020 |
| CN | 112469469 A | 3/2021 |
| CN | 112822992 A | 5/2021 |
| DE | 4412278 A1 | 10/1995 |

(56) References Cited

FOREIGN PATENT DOCUMENTS

| | | |
|---|---|---|
| EP | 0301790 A2 | 2/1989 |
| EP | 1345210 A2 | 9/2003 |
| EP | 1408443 B1 | 10/2006 |
| EP | 2 198 521 B1 | 6/2012 |
| EP | 2541763 A1 | 1/2013 |
| EP | 2733578 A2 | 5/2014 |
| EP | 2 959 394 A1 | 12/2015 |
| EP | 3 104 737 A1 | 12/2016 |
| EP | 3200051 A1 | 8/2017 |
| EP | 3487395 A1 | 5/2019 |
| EP | 2959394 B1 | 5/2021 |
| JP | S61198892 A | 9/1986 |
| JP | H05-277080 A | 10/1993 |
| JP | H07248873 A | 9/1995 |
| JP | 3103427 B2 | 10/2000 |
| JP | 2002287869 A | 10/2002 |
| JP | 2003303047 A | 10/2003 |
| JP | 2005-095561 A | 4/2005 |
| JP | 2005352739 A | 12/2005 |
| JP | 2008192004 A | 8/2008 |
| JP | 2009050679 A | 3/2009 |
| JP | 2010-520561 A | 6/2010 |
| JP | 2013160905 A | 8/2013 |
| JP | WO-2014155288 A2 | 10/2014 |
| JP | WO-2015063520 A1 | 5/2015 |
| JP | 2016-507851 A | 3/2016 |
| JP | 2017-509386 A | 4/2017 |
| JP | 2019023941 A | 2/2019 |
| JP | 2021072136 A | 5/2021 |
| KR | 20110040165 A | 4/2011 |
| KR | 20120094870 A | 8/2012 |
| KR | 20120097997 A | 9/2012 |
| KR | 2015-0123254 A | 11/2015 |
| KR | 2016-0121552 A | 10/2016 |
| KR | 20170067873 A | 6/2017 |
| KR | 20170107283 A | 9/2017 |
| KR | 10-1790147 B1 | 10/2017 |
| WO | 9527341 A1 | 10/1995 |
| WO | 2006086504 A2 | 8/2006 |
| WO | 2008/109248 A2 | 9/2008 |
| WO | 2009/042313 A1 | 4/2009 |
| WO | 2010104879 A2 | 9/2010 |
| WO | WO-2011011750 A1 | 1/2011 |
| WO | 2011070554 A2 | 6/2011 |
| WO | 2012155157 A1 | 11/2012 |
| WO | 2014/130871 A1 | 8/2014 |
| WO | 2014/186370 A1 | 11/2014 |
| WO | 2014/194257 A1 | 12/2014 |
| WO | 2014/197443 A1 | 12/2014 |
| WO | 2015/027089 A1 | 2/2015 |
| WO | 2015/073713 A1 | 5/2015 |
| WO | 2015/081113 A1 | 6/2015 |
| WO | 2015100172 A1 | 7/2015 |
| WO | 2015/123445 A1 | 8/2015 |
| WO | WO-2015123775 A1 | 8/2015 |
| WO | 2015/199747 A1 | 12/2015 |
| WO | 2015184760 A1 | 12/2015 |
| WO | 2015192117 A1 | 12/2015 |
| WO | 2016/041088 A1 | 3/2016 |
| WO | 2017/062544 A1 | 4/2017 |
| WO | 2017075611 A1 | 5/2017 |
| WO | 2017/092225 | 6/2017 |
| WO | 2017092225 A1 | 6/2017 |
| WO | 2017/120669 A1 | 7/2017 |
| WO | 2017/172185 A1 | 10/2017 |
| WO | 2017208167 A1 | 12/2017 |
| WO | 2018022602 A1 | 2/2018 |
| WO | 2018098046 A2 | 5/2018 |
| WO | 2019099758 A1 | 5/2019 |
| WO | 2019147953 A1 | 8/2019 |
| WO | 2019147958 A1 | 8/2019 |
| WO | 2019147996 A1 | 8/2019 |
| WO | 2019217419 A2 | 11/2019 |
| WO | 2019226259 A1 | 11/2019 |
| WO | 2019231911 A1 | 12/2019 |
| WO | 2020047429 A1 | 3/2020 |
| WO | 2020061440 A1 | 3/2020 |
| WO | 2020061451 A1 | 3/2020 |
| WO | 2020072915 A1 | 4/2020 |

OTHER PUBLICATIONS

International Preliminary Report on Patentability for International Application No. PCT/US2018/056768, dated Apr. 30, 2020, 7 pages.
International Search Report and Written Opinion for International Application No. PCT/US2017/043686 dated Oct. 6, 2017.
International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.

(56) References Cited

OTHER PUBLICATIONS

Li et al., Motor Function Evaluation of Hemiplegic Upper-Extremities Using Data Fusion from Wearable Inertial and Surface EMG Sensors. Sensors. MDPI. 2017;17(582):1-17.
Mcintee, A Task Model of Free-Space Movement-Based Geastures. Dissertation. Graduate Faculty of North Carolina State University. Computer Science. 2016. 129 pages.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US19/20065 dated May 16, 2019.
Arkenbout et al., Robust Hand Motion Tracking through Data Fusion of 5DT Data Glove and Nimble VR Kinect Camera Measurements. Sensors. 2015;15:31644-71.
Davoodi et al., Development of a Physics-Based Target Shooting Game to Train Amputee Users of Multijoint Upper Limb Prostheses. Presence. Massachusetts Institute of Technology. 2012;21(1):85-95.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.

Hauschild et al., A Virtual Reality Environment for Designing and Fitting Neural Prosthetic Limbs. IEEE Transactions on Neural Systems and Rehabilitation Engineering. 2007;15(1):9-15.
Lee et al., Motion and Force Estimation System of Human Fingers. Journal of Institute of Control, Robotics and Systems. 2011;17(10):1014-1020.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
Mendes et al., Sensor Fusion and Smart Sensor in Sports and Biomedical Applications. Sensors. 2016;16(1569):1-31.
Sartori et al., Neural Data-Driven Musculoskeletal Modeling for Personalized Neurorehabilitation Technologies. IEEE Transactions on Biomedical Engineering. 2016;63(5):879-93.
Tibold R., et al., "Prediction of Muscle Activity during Loaded Movements of the Upper Limb," Journal of NeuroEngineering Rehabilitation, 2015 vol. 12, No. 6, DOI: https://doi.org/10.1186/1743-0003-12-6, 12 pages.
Non-Final Office Action dated Dec. 30, 2019 for U.S. Appl. No. 16/593,446, filed Oct. 4, 2019, 43 pages.
Non-Final Office Action dated Jun. 30, 2016 for U.S. Appl. No. 14/505,836, filed Oct. 3, 2014, 37 Pages.
Non-Final Office Action dated Oct. 30, 2019 for U.S. Appl. No. 15/882,858, filed Jan. 29, 2018, 22 Pages.
Notice of Allowance dated Nov. 2, 2020 for U.S. Appl. No. 15/974,454, filed May 8, 2018, 24 Pages.
Notice of Allowance dated Nov. 4, 2019 for U.S. Appl. No. 15/974,384, filed May 8, 2018, 39 Pages.
Notice of Allowance dated Feb. 6, 2020 for U.S. Appl. No. 16/424,144, filed May 28, 2019, 28 Pages.
Notice of Allowance dated Feb. 9, 2022 for U.S. Appl. No. 15/882,858, filed Jan. 29, 2018, 9 pages.
Notice of Allowance dated Nov. 10, 2021 for U.S. Appl. No. 15/882,858, filed Jan. 29, 2018, 6 pages.
Notice of Allowance dated Jul. 15, 2021 for U.S. Appl. No. 15/882,858, filed Jan. 29, 2018, 2 pages.
Notice of Allowance dated Dec. 16, 2020 for U.S. Appl. No. 16/593,446, filed Oct. 4, 2019, 44 pages.
Notice of Allowance dated May 18, 2020 for U.S. Appl. No. 16/258,279, filed Jan. 25, 2019, 42 Pages.
Notice of Allowance dated May 18, 2022 for U.S. Appl. No. 15/882,858, filed Jan. 29, 2018, 10 pages.
Notice of Allowance dated Aug. 19, 2020 for U.S. Appl. No. 16/557,427, filed Aug. 30, 2019, 22 Pages.
Notice of Allowance dated Jul. 19, 2019 for U.S. Appl. No. 16/258,409, filed Jan. 25, 2019, 36 Pages.
Notice of Allowance dated May 20, 2020 for U.S. Appl. No. 16/389,419, filed Apr. 19, 2019, 28 Pages.
Notice of Allowance dated Aug. 22, 2022 for U.S. Appl. No. 15/882,858, filed Jan. 29, 2018, 9 pages.
Notice of Allowance dated Oct. 22, 2021 for U.S. Appl. No. 15/882,858, filed Jan. 29, 2018, 8 pages.
Notice of Allowance dated Aug. 23, 2021 for U.S. Appl. No. 15/974,430, filed May 8, 2018, 12 pages.
Notice of Allowance dated Dec. 23, 2020 for U.S. Appl. No. 15/659,072, filed Jul. 25, 2017, 26 Pages.
Notice of Allowance dated Jun. 28, 2021 for U.S. Appl. No. 15/882,858, filed Jan. 29, 2018, 18 pages.
Notice of Allowance dated Jul. 31, 2019 for U.S. Appl. No. 16/257,979, filed Jan. 25, 2019, 22 Pages.
Office action for European Application No. 17835112.8, dated Feb. 11, 2022, 11 Pages.
Office Action for European Patent Application No. 19743717.1, dated Apr. 11, 2022, 10 pages.
Partial Supplementary European Search Report for European Application No. 18879156.0, dated Dec. 7, 2020, 9 pages.
Picard R.W., et al., "Affective Wearables," Proceedings of the IEEE 1st International Symposium on Wearable Computers, ISWC, Cambridge, MA, USA, Oct. 13-14, 1997, pp. 90-97.

(56) References Cited

OTHER PUBLICATIONS

Preinterview First Office Action dated Jun. 24, 2020 for U.S. Appl. No. 16/785,680, filed Feb. 10, 2020, 90 Pages.
Rekimoto J., "GestureWrist and GesturePad: Unobtrusive Wearable Interaction Devices," ISWC Proceedings of the 5th IEEE International Symposium on Wearable Computers, 2001, 7 pages.
Sato M., et al., "Touche: Enhancing Touch Interaction on Humans, Screens, Liquids, and Everyday Objects," CHI, Austin, Texas, May 5-10, 2012, 10 pages.
Ueno A., et al., "A Capacitive Sensor System for Measuring Laplacian Electromyogram through Cloth: A Pilot Study," Proceedings of the 29th Annual International Conference of the IEEE EMBS, Cite Internationale, Lyon, France, Aug. 23-26, 2007, pp. 5731-5734.
Ueno A., et al., "Feasibility of Capacitive Sensing of Surface Electromyographic Potential through Cloth," Sensors and Materials, 2012, vol. 24 (6), pp. 335-346.
Valero-Cuevas F.J., et al., "Computational Models for Neuromuscular Function," IEEE Reviews in Biomedical Engineering, 2009, vol. 2, NIH Public Access Author Manuscript [online], Jun. 16, 2011 [Retrieved on Jul. 29, 2019], 52 pages, Retrieved from the Internet: URL: https://www.ncbi.nlm.nih.gov/pmc/articles/PMC3116649/.
Wittevrongel B., et al., "Spatiotemporal Beamforming: A Transparent and Unified Decoding Approach to Synchronous Visual Brain-Computer Interfacing," Frontiers in Neuroscience, Nov. 15, 2017, vol. 11, Article No. 630, 13 Pages.
Xiong A., et al., "A Novel HCI based on EMG and IMU," Proceedings of the 2011 IEEE International Conference on Robotics and Biomimetics, Phuket, Thailand, Dec. 7-11, 2011, pp. 2653-2657.
Xu Z., et al., "Hand Gesture Recognition and Virtual Game Control Based on 3D Accelerometer and EMG Sensors," Proceedings of the 14th International Conference on Intelligent User Interfaces, D211 Sanibel Island, Florida, Feb. 8-11, 2009, pp. 401-406.
Yang Z., et al., "Surface EMG Based Handgrip Force Predictions Using Gene Expression Programming," Neurocomputing, 2016, vol. 207, pp. 568-579.
Zacharaki E.I., et al., "Spike Pattern Recognition by Supervised Classification in Low Dimensional Embedding Space," Brain Informatics, 2016, vol. 3, pp. 73-83.
Zhang X., et al., "A Framework for Hand Gesture Recognition Based on Accelerometer and EMG Sensors," IEEE Transactions on Systems, Man, and Cybernetics—Part A: Systems and Humans, Nov. 2011, vol. 41 (6), pp. 1064-1076.
Final Office Action dated Feb. 4, 2021 for U.S. Appl. No. 15/882,858, filed Jan. 29, 2018, 42 Pages.
Final Office Action dated Jun. 5, 2020 for U.S. Appl. No. 16/557,427, filed Aug. 30, 2019, 95 Pages.
Final Office Action dated Oct. 8, 2020 for U.S. Appl. No. 16/557,342, filed Aug. 30, 2019, 73 Pages.
Final Office Action dated Apr. 9, 2020 for U.S. Appl. No. 15/974,454, filed May 8, 2018, 19 Pages.
Final Office Action dated Dec. 11, 2019 for U.S. Appl. No. 15/974,430, filed May 8, 2018, 30 Pages.
Final Office Action dated Jan. 13, 2021 for U.S. Appl. No. 16/577,207, filed Sep. 20, 2019, 91 Pages.
Final Office Action dated Dec. 18, 2019 for U.S. Appl. No. 16/258,279, filed Jan. 25, 2019, 45 Pages.
Final Office Action dated Feb. 19, 2021 for U.S. Appl. No. 16/258,279, filed Jan. 25, 2019, 58 Pages.
Final Office Action dated Sep. 23, 2020 for U.S. Appl. No. 15/816,435, filed Nov. 17, 2017, 70 Pages.
Final Office Action dated Jan. 28, 2020 for U.S. Appl. No. 16/557,342, filed Aug. 30, 2019, 15 Pages.
Final Office Action dated Jul. 28, 2017 for U.S. Appl. No. 14/505,836, filed Oct. 3, 2014, 52 Pages.
Final Office Action dated Jun. 28, 2021 for U.S. Appl. No. 16/557,342, filed Aug. 30, 2019, 11 Pages.
Final Office Action dated Nov. 29, 2019 for U.S. Appl. No. 15/659,072, filed Jul. 25, 2017, 36 Pages.
Final Office Action dated Nov. 29, 2019 for U.S. Appl. No. 16/353,998, filed Mar. 14, 2019, 33 Pages.
Fong H.C., et al., "PepperGram With Interactive Control," 22nd International Conference Onvirtual System & Multimedia (VSMM), Oct. 17, 2016, 5 pages.
Ghasemzadeh H., et al., "A Body Sensor Network With Electromyogram and Inertial Sensors: Multimodal Interpretation of Muscular Activities," IEEE Transactions on Information Technology in Biomedicine, Mar. 2010, vol. 14 (2), pp. 198-206.
Gopura R.A.R.C., et al., "A Human Forearm and Wrist Motion Assist Exoskeleton Robot With EMG-Based Fuzzy-Neuro Control," Proceedings of the 2nd Biennial IEEE/RAS-EMBS International Conference on Biomedical Robotics and Biomechatronics, Oct. 19-22, 2008, 6 pages.
Gourmelon L., et al., "Contactless Sensors for Surface Electromyography," Proceedings of the 28th IEEE EMBS Annual International Conference, New York City, NY, Aug. 30-Sep. 3, 2006, pp. 2514-2517.
International Search Report and Written Opinion for International Application No. PCT/US2014/017799, dated May 16, 2014, 9 pages.
International Search Report and Written Opinion for International Application No. PCT/US2014/037863, dated Aug. 21, 2014, 10 pages.
International Preliminary Report on Patentability for International Application No. PCT/US2019/031114, dated Nov. 19, 2020, 16 pages.
International Preliminary Report on Patentability for International Application No. PCT/US2019/049094, dated Mar. 11, 2021, 24 Pages.
International Preliminary Report on Patentability for International Application No. PCT/US2019/052151, dated Apr. 1, 2021, 9 pages.
International Preliminary Report on Patentability for International Application No. PCT/US2014/017799, dated Sep. 3, 2015, 8 Pages.
International Preliminary Report on Patentability for International Application No. PCT/US2014/037863, dated Nov. 26, 2015, 8 pages.
International Preliminary Report on Patentability for International Application No. PCT/US2014/052143, dated Mar. 3, 2016, 7 pages.
International Preliminary Report on Patentability for International Application No. PCT/US2014/067443, dated Jun. 9, 2016, 7 pages.
International Preliminary Report on Patentability for International Application No. PCT/US2015/015675, dated Aug. 25, 2016, 8 Pages.
International Preliminary Report on Patentability for International Application No. PCT/US2018/061409, dated May 28, 2020, 10 pages.
International Preliminary Report on Patentability for International Application No. PCT/US2019/015174, dated Aug. 6, 2020, 7 pages.
International Preliminary Report on Patentability for International Application No. PCT/US2019/015183, dated Aug. 6, 2020, 7 pages.
International Preliminary Report on Patentability for International Application No. PCT/US2019/015238, dated Aug. 6, 2020, 7 pages.
International Preliminary Report on Patentability for International Application No. PCT/US2019/028299, dated Dec. 10, 2020, 11 pages.
International Preliminary Report on Patentability for International Application No. PCT/US2019/034173, dated Dec. 10, 2020, 9 pages.
International Preliminary Report on Patentability for International Application No. PCT/US2019/046351, dated Feb. 25, 2021, 8 pages.
International Preliminary Report on Patentability for International Application No. PCT/US2019/052131, dated Apr. 1, 2021, 8 pages.
International Preliminary Report on Patentability for International Application No. PCT/US2019/054716, dated Apr. 15, 2021, 10 pages.
International Preliminary Report on Patentability for International Application No. PCT/US2019/061759, dated May 27, 2021, 12 pages.
International Preliminary Report on Patentability for International Application No. PCT/US2019/063587, dated Jun. 10, 2021, 13 pages.

(56) References Cited

OTHER PUBLICATIONS

International Preliminary Report on Patentability for International Application No. PCT/US2020/049274, dated Mar. 17, 2022, 14 pages.
International Preliminary Report on Patentability for International Application No. PCT/US2020/061392, dated Jun. 9, 2022, 11 pages.
International Search Report and Written Opinion for International Application No. PCT/US2014/052143, dated Nov. 21, 2014, 8 Pages.
International Search Report and Written Opinion for International Application No. PCT/US2014/067443, dated Feb. 27, 2015, 8 pages.
International Search Report and Written Opinion for International Application No. PCT/US2015/015675, dated May 27, 2015, 9 Pages.
International Search Report and Written Opinion for International Application No. PCT/US2019/028299, dated Aug. 9, 2019, 12 pages.
International Search Report and Written Opinion for International Application No. PCT/US2019/031114, dated Dec. 20, 2019, 18 Pages.
International Search Report and Written Opinion for International Application No. PCT/US2019/034173, dated Sep. 18, 2019, 10 Pages.
International Search Report and Written Opinion for International Application No. PCT/US2019/037302, dated Oct. 11, 2019, 13 Pages.
International Search Report and Written Opinion for International Application No. PCT/US2019/042579, dated Oct. 31, 2019, 8 Pages.
Al-Jumaily A., et al., "Electromyogram(EMG) Driven System based Virtual Reality for Prosthetic and Rehabilitation Devices," Proceedings of the 11th Internationalconference on Information Integration Andweb-Based Applications & Services, Jan. 1, 2009, pp. 582-586.
Al-Mashhadany Y.I., "Inverse Kinematics Problem (IKP) of 6-DOF Manipulator by Locally Recurrent Neural Networks (LRNNs)," Management and Service Science (MASS), International Conference on Management and Service Science., IEEE, Aug. 24, 2010, 5 pages.
Al-Timemy A.H., et al., "Improving the Performance Against Force Variation of EMG Controlled Multifunctional Upper-Limb Prostheses for Transradial Amputees," IEEE Transactions on Neural Systems and Rehabilitation Engineering, Jun. 2016, vol. 24 (6), 12 Pages.
Berenzweig A., et al., "Wearable Devices and Methods for Improved Speech Recognition," U.S. Appl. No. 16/785,680, filed Feb. 10, 2020, 67 pages.
Brownlee J., "Finite State Machines (FSM): Finite State Machines as a Control Technique in Artificial Intelligence (AI)," FSM, Jun. 2002, 12 pages.
Cannan J., et al., "A Wearable Sensor Fusion Armband for Simple Motion Control and Selection for Disabled and Non-Disabled Users," Computer Science and Electronic Engineering Conference, IEEE, Sep. 12, 2012, pp. 216-219, XP032276745.
Communication Pursuant to Article 94(3) for European Patent Application No. 17835112.8, dated Dec. 14, 2020, 6 Pages.
Communication Pursuant to Rule 164(1) EPC, Partial Supplementary European Search Report for European Application No. 14753949.8, dated Sep. 30, 2016, 7 pages.
Co-pending U.S. Appl. No. 15/659,072, inventors Patrick; Kaifosh et al., filed Jul. 25, 2017.
Co-pending U.S. Appl. No. 15/816,435, inventors Ning; Guo et al., filed Nov. 17, 2017.
Co-pending U.S. Appl. No. 15/882,858, inventors Stephen; Lake et al., filed Jan. 29, 2018.
Co-pending U.S. Appl. No. 15/974,430, inventors Adam; Berenzweig et al., filed May 8, 2018.
Co-pending U.S. Appl. No. 16/353,998, inventors Patrick; Kaifosh et al., filed Mar. 14, 2019.
Co-pending U.S. Appl. No. 16/557,383, inventors Adam; Berenzweig et al., filed Aug. 30, 2019.
Co-pending U.S. Appl. No. 16/557,427, inventors Adam; Berenzweig et al., filed Aug. 30, 2019.
Co-Pending U.S. Appl. No. 15/974,430, filed May 8, 2018, 44 Pages.
Co-Pending U.S. Appl. No. 16/353,998, filed Mar. 14, 2019, 43 pages.
Co-Pending U.S. Appl. No. 16/557,383, filed Aug. 30, 2019, 94 Pages.
Co-Pending U.S. Appl. No. 16/557,427, filed Aug. 30, 2019, 93 Pages.
Co-Pending U.S. Appl. No. 16/577,207, filed Sep. 20, 2019, 67 Pages.
Co-Pending U.S. Appl. No. 14/505,836, filed Oct. 3, 2014, 59 Pages.
Co-Pending U.S. Appl. No. 15/816,435, filed Nov. 17, 2017, 24 Pages.
Co-Pending U.S. Appl. No. 15/882,858, filed Jan. 29, 2018, 54 Pages.
Co-Pending U.S. Appl. No. 15/974,384, filed May 8, 2018, 44 Pages.
Co-Pending U.S. Appl. No. 15/974,454, filed May 8, 2018, 45 Pages.
Co-Pending U.S. Appl. No. 16/557,342, filed Aug. 30, 2019, 93 Pages.
Corazza S., et al.,"A Markerless Motion Capture System to Study Musculoskeletal Biomechanics: Visual Hull and Simulated Annealing Approach," Annals of Biomedical Engineering, Jul. 2006, vol. 34 (6), pp. 1019-1029, [Retrieved on Dec. 11, 2019], 11 pages, Retrieved from the Internet: URL: https://www.researchgate.net/publication/6999610_A_Markerless_Motion_Capture_System_to_Study_Musculoskeletal_Biomechanics_Visual_Hull_and_Simulated_Annealing_Approach.
Costanza E., et al., "EMG as a Subtle Input Interface for Mobile Computing," Mobile HCI, LNCS 3160, 2004, pp. 426-430.
Costanza E., et al., "Toward Subtle Intimate Interfaces for Mobile Devices Using an EMG Controller," CHI, Proceedings of the SIGCHI Conference on Human Factors in Computing Systems, Apr. 2-7, 2005, pp. 481-489.
Cote-Allard U., et al., "Deep Learning for Electromyographic Hand Gesture Signal Classification Using Transfer Learning," IEEE Transactions on Neural Systems and Rehabilitation Engineering, Jan. 26, 2019, vol. 27 (4), 11 Pages.
European Search Report for European Application No. 19861903.3, dated Oct. 12, 2021, 2 pages.
European Search Report for European Application No. 19863248.1, dated Oct. 19, 2021, 2 pages.
European Search Report for European Application No. 19868789.9, dated May 9, 2022, 9 pages.
European Search Report for European Application No. 19890394.0, dated Apr. 29, 2022, 9 pages.
Extended European Search Report for European Application No. 18879156.0, dated Mar. 12, 2021, 11 pages.
Extended European Search Report for European Application No. 19743717.1, dated Mar. 3, 2021, 12 pages.
Extended European Search Report for European Application No. 19744404.5, dated Mar. 29, 2021, 11 pages.
Extended European Search Report for European Application No. 19799947.7, dated May 26, 2021, 10 pages.
Extended European Search Report for European Application No. 17835111.0, dated Nov. 21, 2019, 6 pages.
Extended European Search Report for European Application No. 17835112.8, dated Feb. 5, 2020, 17 pages.
Extended European Search Report for European Application No. 17835140.9, dated Nov. 26, 2019, 10 Pages.
Extended European Search Report for European Application No. 19806723.3, dated Jul. 7, 2021, 13 pages.
Extended European Search Report for European Application No. 19810524.9, dated Mar. 17, 2021, 11 pages.
Extended European Search Report for European Application No. 19850130.6, dated Sep. 1, 2021, 14 Pages.

(56) References Cited

OTHER PUBLICATIONS

Extended European Search Report for European Application No. 19855191.3, dated Dec. 6, 2021, 11 pages.
Extended European Search Report for European Application No. 19883839.3, dated Dec. 15, 2021, 7 pages.
Final Office Action dated Jun. 2, 2020 for U.S. Appl. No. 15/882,858, filed Jan. 29, 2018, 127 Pages.
Final Office Action dated Jun. 2, 2020 for U.S. Appl. No. 16/557,383, filed Aug. 30, 2019, 66 Pages.
Final Office Action dated Nov. 3, 2020 for U.S. Appl. No. 15/974,430, filed May 8, 2018, 27 Pages.
Final Office Action dated Feb. 4, 2020 for U.S. Appl. No. 16/577,207, filed Sep. 20, 2019, 76 Pages.
International Search Report and Written Opinion for International Application No. PCT/US2019/046351, dated Nov. 7, 2019, 9 pages.
International Search Report and Written Opinion for International Application No. PCT/US2019/049094, dated Jan. 9, 2020, 27 Pages.
International Search Report and Written Opinion for International Application No. PCT/US2019/052131, dated Dec. 6, 2019, 8 pages.
International Search Report and Written Opinion for International Application No. PCT/US2019/052151, dated Jan. 15, 2020, 10 pages.
International Search Report and Written Opinion for International Application No. PCT/US2019/054716, dated Dec. 20, 2019, 11 Pages.
International Search Report and Written Opinion for International Application No. PCT/US2019/061759, dated Jan. 29, 2020, 12 pages.
International Search Report and Written Opinion for International Application No. PCT/US2019/063587, dated Mar. 25, 2020, 16 pages.
International Search Report and Written Opinion for International Application No. PCT/US2020/025735, dated Jun. 22, 2020, 10 pages.
International Search Report and Written Opinion for International Application No. PCT/US2020/025772, dated Aug. 3, 2020, 11 pages.
International Search Report and Written Opinion for International Application No. PCT/US2020/025797, dated Jul. 9, 2020, 10 pages.
International Search Report and Written Opinion for International Application No. PCT/US2020/049274, dated Feb. 1, 2021, 17 pages.
International Search Report and Written Opinion for International Application No. PCT/US2020/061392, dated Mar. 12, 2021, 12 pages.
Invitation to Pay Additional Fees for International Application No. PCT/US2019/031114, dated Aug. 6, 2019, 7 pages.
Invitation to Pay Additional Fees for International Application No. PCT/US2019/049094, dated Oct. 24, 2019, 2 Pages.
Kainz et al., "Approach to Hand Tracking and Gesture Recognition Based on Depth-Sensing Cameras and EMG Monitoring," Acta Informatica Pragensia, vol. 3, Jan. 1, 2014, pp. 104-112, Retrieved from the Internet: URL: https://aip.vse.cz/pdfs/aip/2014/01/08.pdf.
Kipke D.R., et al., "Silicon-Substrate Intracortical Microelectrode Arrays for Long-Term Recording of Neuronal Spike Activity in Cerebral Cortex," IEEE Transactions on Neural Systems and Rehabilitation Engineering, Jun. 2003, vol. 11(2), 5 pages, Retrieved on Oct. 7, 2019 [Oct. 7, 2019] Retrieved from the Internet: URL: https://www.ece.uvic.ca/-bctill/papers/neurimp/Kipke_etal_2003_01214707.pdf.
Marcard T.V., et al., "Sparse Inertial Poser: Automatic 3D Human Pose Estimation from Sparse IMUs," arxiv.org, Computer Graphics Forum, 2017, vol. 36 (2), 12 pages, XP080759137.
Mohamed O.H., "Homogeneous Cognitive Based Biometrics for Static Authentication," Dissertation submitted to University of Victoria, Canada, 2010, [last accessed Oct. 11, 2019], 149 pages, Retrieved from the Internet: URL: http://hdl.handle.net/1828/321.
Morris D., et al., "Emerging Input Technologies for Always-Available Mobile Interaction," Foundations and Trends in Human-Computer Interaction, 2010, vol. 4 (4), pp. 245-316.
Naik G.R., et al., "Real-Time Hand Gesture Identification for Human Computer Interaction Based on ICA of Surface Electromyogram," IADIS International Conference Interfaces and Human Computer Interaction, 2007, pp. 83-90.
Non-Final Office Action dated Mar. 2, 2021 for U.S. Appl. No. 15/974,430, filed May 8, 2018, 32 Pages.
Non-Final Office Action dated Sep. 2, 2020 for U.S. Appl. No. 15/882,858, filed Jan. 29, 2018, 66 Pages.
Non-Final Office Action dated Aug. 3, 2020 for U.S. Appl. No. 16/593,446, filed Oct. 4, 2019, 44 pages.
Non-Final Office Action dated Jun. 3, 2021 for U.S. Appl. No. 15/816,435, filed Nov. 17, 2017, 32 Pages.
Non-Final Office Action dated Jun. 5, 2020 for U.S. Appl. No. 15/659,072, filed Jul. 25, 2017, 59 Pages.
Non-Final Office Action dated Sep. 6, 2019 for U.S. Appl. No. 16/424,144, filed May 28, 2019, 11 Pages.
Non-Final Office Action dated Feb. 8, 2021 for U.S. Appl. No. 16/557,342, filed Aug. 30, 2019, 11 Pages.
Non-Final Office Action dated Oct. 8, 2020 for U.S. Appl. No. 16/577,207, filed Sep. 20, 2019, 51 Pages.
Non-Final Office Action dated Apr. 9, 2019 for U.S. Appl. No. 16/258,409, filed Jan. 25, 2019, 71 Pages.
Non-Final Office Action dated Aug. 11, 2021 for U.S. Appl. No. 16/577,207, filed Sep. 20, 2019, 35 Pages.
Non-Final Office Action dated Jun. 13, 2019 for U.S. Appl. No. 16/258,279, filed Jan. 25, 2019, 38 Pages.
Non-Final Office Action dated Jun. 15, 2020 for U.S. Appl. No. 16/557,342, filed Aug. 30, 2019, 46 Pages.
Non-Final Office Action dated Jan. 16, 2020 for U.S. Appl. No. 16/389,419, filed Apr. 19, 2019, 26 Pages.
Non-Final Office Action dated May 16, 2019 for U.S. Appl. No. 15/974,384, filed May 8, 2018, 13 Pages.
Non-Final Office Action dated May 16, 2019 for U.S. Appl. No. 15/974,430, filed May 8, 2018, 12 Pages.
Non-Final Office Action dated Nov. 19, 2019 for U.S. Appl. No. 16/577,207, filed Sep. 20, 2019, 32 Pages.
Non-Final Office Action dated Aug. 20, 2020 for U.S. Appl. No. 15/974,454, filed May 8, 2018, 59 Pages.
Non-Final Office Action dated Dec. 20, 2019 for U.S. Appl. No. 15/974,454, filed May 8, 2018, 41 Pages.
Non-Final Office Action dated Jan. 22, 2020 for U.S. Appl. No. 15/816,435, filed Nov. 17, 2017, 35 Pages.
Non-Final Office Action dated Oct. 22, 2019 for U.S. Appl. No. 16/557,342, filed Aug. 30, 2019, 16 Pages.
Non-Final Office Action dated Dec. 23, 2019 for U.S. Appl. No. 16/557,383, filed Aug. 30, 2019, 53 Pages.
Non-Final Office Action dated Dec. 23, 2019 for U.S. Appl. No. 16/557,427, filed Aug. 30, 2019, 52 Pages.
Non-Final Office Action dated Feb. 23, 2017 for U.S. Appl. No. 14/505,836, filed Oct. 3, 2014, 54 Pages.
Non-Final Office Action dated Jul. 23, 2020 for U.S. Appl. No. 16/593,446, filed Oct. 4, 2019, 28 pages.
Non-Final Office Action dated May 24, 2019 for U.S. Appl. No. 16/353,998, filed Mar. 14, 2019, 20 Pages.
Non-Final Office Action dated May 26, 2020 for U.S. Appl. No. 16/353,998, filed Mar. 14, 2019, 60 Pages.
Non-Final Office Action dated Nov. 27, 2020 for U.S. Appl. No. 16/258,279, filed Jan. 25, 2019, 44 Pages.
Non-Final Office Action dated Apr. 29, 2019 for U.S. Appl. No. 16/257,979, filed Jan. 25, 2019, 63 Pages.
Non-Final Office Action dated Apr. 30, 2019 for U.S. Appl. No. 15/659,072, filed Jul. 25, 2017, 99 Pages.
Non-Final Office Action dated Apr. 30, 2020 for U.S. Appl. No. 15/974,430, filed May 8, 2018, 57 Pages.
Amitai Y., "P-27: A Two-Dimensional Aperture Expander for Ultra-Compact, High-Performance Head-Worn Displays," SID Symposium Digest of Technical Papers, 2005, vol. 36 (1), pp. 360-363.
Ayras P., et al., "Exit Pupil Expander With a Large Field of View Based on Diffractive Optics," Journal of the SID, 2009, vol. 17 (8), pp. 659-664.

(56) References Cited

OTHER PUBLICATIONS

Bailey et al., Wearable Muscle Interface Systems, Devices and Methods That Interact With Content Displayed on an Electronic Display, Office Action dated Mar. 31, 2015, for U.S. Appl. No. 14/155,107, 17 pages.
Bailey et al., "Muscle Interface Device and Method for Interacting With Content Displayed on Wearable Head Mounted Displays," Amendment filed Aug. 25, 2015, for U.S. Appl. No. 14/155,087, 10 pages.
Bailey et al., "Muscle Interface Device and Method for Interacting Wth Content Displayed on Wearable Head Mounted Displays," Amendment filed Aug. 9, 2016, for U.S. Appl. No. 14/155,087, 8 pages.
Bailey et al., "Muscle Interface Device and Method for Interacting With Content Displayed on Wearable Head Mounted Displays," Amendment filed May 17, 2016, for U.S. Appl. No. 14/155,087, 13 pages.
Bailey et al., "Muscle Interface Device and Method for Interacting With Content Displayed on Wearable Head Mounted Displays," Office Action dated Feb. 17, 2016, for U.S. Appl. No. 14/155,087, 16 pages.
Bailey et al., "Muscle Interface Device and Method for Interacting With Content Displayed on Wearable Head Mounted Displays," Office Action dated Jul. 20, 2015, for U.S. Appl. No. 14/155,087, 14 pages.
Bailey et al., "Muscle Interface Device and Method for Interacting Wth Content Displayed on Wearable Head Mounted Displays," Office Action dated Jul. 8. 2016, for U.S. Appl. No. 14/155,087, 16 pages.
Bailey et al., "Muscle Interface Device and Method for Interacting With Content Displayed on Wearable Head Mounted Displays," Office Action dated Mar. 31, 2015, for U.S. Appl. No. 14/155,107, 15 pages.
Bailey et al., "Muscle Interface Device and Method for Interacting With Content Displayed on Wearable Head Mounted Displays," Preliminary Amendment filed Jan. 28, 2014, for U.S. Appl. No. 14/155,107, 8 pages.
Bailey et al., "Wearable Muscle Interface Systems, Devices and Methods That Interact Wth. Content Displayed on an Electronic Display," Amendment filed Aug. 9, 2016, for U.S. Appl. No. 14/155,107, 8 pages.
Bailey et al., "Wearable Muscle Interface Systems, Devices and Methods That Interact With Content Displayed on an Electronic Display," Amendment filed May 11, 2016, for U.S. Appl. No. 14/155,107, 15 pages.
Bailey et al., Wearable Muscle Interface Systems, Devices and Methods That Interact With Content Displayed on an Electronic Display/Office Action dated Feb. 11, 2016, for U.S. Appl. No. 14/155,107, 20 pages.
Bailey et al.. Wearable Muscle Interface Systems, Devices and Methods That Interact With Content Displayed on an Electronic Display, Office Action dated Jul. 16, 2015, for U.S. Appl. No. 14/155,107, 20 pages.
Bailey et al., Wearable Muscle Interface Systems. Devices and Methods That Interact With Content Displayed on an Electronic Display/ Office Action dated Jul. 8, 2016, for U.S. Appl. No. 14/155,107, 21 pages.
Chellappan K.V., et al., "Laser-Based Displays: A Review," Applied Optics, Sep. 1, 2010, vol. 49 (25), pp. F79-F98.
Co-Pending U.S. Appl. No. 16/430,299, filed Jun. 3, 2019, 42 Pages.
Cui L., et al., "Diffraction From Angular Multiplexing Slanted Volume Hologram Gratings," Optik 2005, vol. 116, pp. 118-122.
Curatu C., et al., "Dual Purpose Lens for an Eye-Tracked Projection Head-Mounted Display," International Optical Design Conference SPIE-OSA, 2006, vol. 6342, pp. 63420X-1-63420X-7.
Curatu C., et al., "Projection-Based Head-Mounted Display With Eye-Tracking Capabilities," Proceedings of SPIE, 2005, vol. 5875, pp. 58750J-1-58750J-9.
Essex D., "Tutorial on Optomechanical Beam Steering Mechanisms," OPTI 521 Tutorial, College of Optical Sciences, University of Arizona, 2006, 8 pages.
Farina D., et al., "The Extraction of Neural Information from the Surface EMG for the Control of Upper-Limb Prostheses: Emerging Avenues and Challenges," IEEE Transactions on Neural Systems Andrehabilitation Engineering, vol. 22, No. 4, Jul. 1, 2014, pp. 797-809.
Fernandez E., et al., "Optimization of a Thick Polyvinyl Alcohol-Acrylamide Photopolymer for Data Storage Using a Combination of Angular and Peristrophic Holographic Multiplexing," Applied Optics, Oct. 10, 2009, Voi. 45 (29), pp. 7661-7666.
Final Office Action dated Jan. 3, 2019 for U.S. Appl. No. 14/465,194, filed Aug. 21, 2014, 61 Pages.
Final Office Action dated Jan. 10, 2018 for U.S. Appl. No. 14/465,194, filed Aug. 21, 2014, 50 Pages.
Final Office Action dated Nov. 18, 2020 for U.S. Appl. No. 14/461,044, filed Aug. 15, 2014, 14 Pages.
Final Office Action dated Oct. 21, 2021 for U.S. Appl. No. 16/899,843, filed Jun. 12, 2020, 29 Pages.
Final Office Action dated Jul. 23, 2021 for U.S. Appl. No. 14/461,044, filed Aug. 15, 2014, 15 Pages.
Final Office Action received for U.S. Appl. No. 14/155,087 dated Dec. 16, 2016, 32 pages.
Final Office Action received for U.S. Appl. No. 14/155,087 dated Jul. 20, 2015, 27 pages.
Final Office Action received for U.S. Appl. No. 14/155,087 dated Jul. 8, 2016, 27 pages.
Final Office Action received for U.S. Appl. No. 14/155,107 dated Nov. 27, 2017, 40 pages.
Final Office Action received for U.S. Appl. No. 14/155,107 dated Dec. 19, 2016, 35 pages.
Final Office Action received for U.S. Appl. No. 14/155,107 dated Jan. 17, 2019, 46 pages.
Final Office Action received for U.S. Appl. No. 14/155,107 dated Jul. 16, 2015, 28 pages.
Final Office Action received for U.S. Appl. No. 14/155,107 dated Jul. 8, 2016, 31 pages.
Final Office Action received for U.S. Appl. No. 14/155,107 dated Nov. 27, 2017, 44 pages.
First Office Action dated Nov. 25, 2020, for Canadian Application No. 2921954, filed Aug. 21, 2014, 4 pages.
Hainich R.R., et al., "Chapter 10: Near-Eye Displays," Displays: Fundamentals & Applications, AK Peters/CRC Press, 2011, 65 pages.
Hornstein S., et al., "Maradin's Micro-Mirror - System Level Synchronization Notes," SID Digest, 2012, pp. 981-984.
"IEEE 100 The Authoritative Dictionary of IEEE Standards Terms," Seventh Edition, Standards Information Network IEEE Press, Dec. 2000, 3 pages.
International Search Report and Written Opinion for International Application No. PCT/US2016/018293, dated Jun. 8, 2016, 17 Pages.
International Search Report and Wrillen Opinion for International Application No. PCT/US2016/018298, dated Jun. 8, 2016, 14 Pages.
International Search Report and Written Opinion for International Application No. PCT/US2016/018299, dated Jun. 8, 2016, 12 Pages.
International Search Report and Wrillen Opinion for International Application No. PCT/US2016/067246, dated Apr. 25, 2017, 10 Pages.
Itoh Y., et al., "Interaction-Free Calibration for Optical See-Through Head-Mounted Displays based on 3D Eye Localization," IEEE Symposium on 3D User Interfaces (3DUI), 2014, pp. 75-82.
Janssen C., "Radio Frequency (RF)," 2013, [Retrieved on Jul. 12, 2017], 2 pages, Retrieved from the Internet: URL: https://web.archive.org/web/20130726153946/https://www.techopedia.com/definition/5083/radio-frequency-rf.
Kessler D.. "Optics of Nearto Eye Displays (NEDs)," Presentation—Oasis, Tel Aviv, Feb. 19, 2013, 37 pages.

(56) References Cited

OTHER PUBLICATIONS

Krees B.C., et al., "Diffractive and Holographic Optics as Optical Combiners in Head Mounted Displays," UbiComp, Zurich, Switzerland, Sep. 8-12, 2013, pp. 1479-1482.
Kress B., et al., "A Review of Head-Mounted Displays (HMD) Technologies and Applications for Consumer Electronics," Proceedings of SPIE, 2013, vol. 8720, pp. 87200A-1-87200A-13.
Kress B., "Optical Architectures for See-Through Wearable Displays," Presentation, Bay Area SID Seminar, Apr. 30, 2014, 156 pages.
Lake et al., "Method and Apparatus for Analyzing Capacitive EMG and IMU Sensor Signals for Gesture Control," Amendment filed Aug. 21, 2015, for U.S. Appl. No. 14/186,878, 13 pages.
Lake et al., "Method and Apparatus for Analyzing Capacitive EMG and IMU Sensor Signals for Gesture Control," Office Action dated Jun. 17, 2015, for U.S. Appl. No. 14/186,878, 13 pages.
Lake et al., "Methods and Apparatus for Analyzing Capacitive EMG and IMU Sensor Signals for Gesture Control," Preliminary Amendment filed May 9, 2014, for U.S. Appl. No. 14/186,878, 9 pages.
Lake et al., "Method and Apparatus for Analyzing Capacitive EMG and IMU Sensor Signals for Gesture Control," U.S. Appl. No. 14/186,889, 29 pages.
Lake et al., "Methods and Devices for Combining Muscle Activity Sensor Signals and Inertial Sensor Signals for Gesture-Based Control," Amendment filed Jan. 8, 2016, for U.S. Appl. No. 14/186,889, 16 pages.
Lake et al.,, "Methods and Devices for Combining Muscle Activity Sensor Signals and Inertial Sensor Signals for Gesture-Based Control," Amendment filed Jul. 13, 2016, for U.S. Appl. No. 14/186,889, 12 pages.
Lake et al., "Methods and Devices for Combining Muscle Activity Sensor Signals and Inertial Sensor Signals for Gesture-Based Control," Office Action dated Jun. 16, 2016, for U.S. Appl. No. 14/186,889, 13 pages.
Lake et al., "Methods and Devices for Combining Muscle Activity Sensor Signals and Inertial Sensor Signals for Gesture-Based Control," Office Action dated Nov. 5, 2015, for U.S. Appl. No. 14/186,889, 11 pages.
Lake et al., "Methods and Devices That Combine Muscle Activity Sensor Signals and Inertial Sensor Signals for Gesture-Based Control," U.S. Appl. No. 14/186,889, filed Feb. 21, 2014, 58 pages.
Levola T., "7.1: Invited Paper: Novel Diffractive Optical Components for Nearto Eye Displays," SID Symposium Digest of Technical Papers, 2006, vol. 37 (1), pp. 64-67.
Liao C.D., et al., "The Evolution of MEMS Displays," IEEE Transactions on Industrial Electronics, Apr. 2009, vol. 56 (4), pp. 1057-1065.
Lippert T.M., "Chapter 6: Display Devices: RSD™ (Retinal Scanning Display)," The Avionics Handbook, CRC Press, 2001, 8 pages.
Majaranta P., et al., "Chapter 3: Eye Tracking and Eye-Based Human-Computer Interaction," Advances in Physiological Computing, Springer-Verlag London, 2014, pp. 39-65.
Merriam-Webster, "Radio Frequencies," download date Jul. 12, 2017, 2 pages, Retrieved from the Internet: URL: https://www.merriam-webster.com/table/coliegiate/radiofre.htm.
Morun C., et al., "Systems, Articles, and Methods for Capacitive Electromyography Sensors," U.S. Appl. No. 16/437,351, filed Jun. 11, 2019, 51 pages.
Non-Final Office Action dated Mar. 1, 2018 for U.S. Appl. No. 15/799,628, filed Oct. 31, 2017, 29 Pages.
Non-Final Office Action dated May 2, 2018 for U.S. Appl. No. 15/799,628, filed Oct. 31, 2017, 25 Pages.
Non-Final Office Action dated Oct. 5, 2022 for U.S. Appl. No. 16/057,573, filed Aug. 7, 2018, 14 pages.
Non-Final Office Action dated Nov. 6, 2018 for U.S. Appl. No. 16/057,573, filed Aug. 7, 2018, 14 Pages.
Non-Final Office Action dated May 7, 2021 for U.S. Appl. No. 17/141,646, filed Jan. 5, 2021, 24 Pages.
Non-Final Office Action dated Oct. 7, 2022 for U.S. Appl. No. 17/141,646, filed Jan. 5, 2021, 6 pages.
Non-Final Office Action dated Sep. 11, 2019 for U.S. Appl. No. 14/465,194, filed Aug. 21, 2014, 72 Pages.
Non-Final Office Action dated May 12, 2022 for U.S. Appl. No. 16/899,843, filed Jun. 12, 2020, 34 Pages.
Non-Final Office Action dated Sep. 14, 2017 for U.S. Appl. No. 14/539,773, filed Nov. 12, 2014, 28 pages.
Non-Final Office Action dated Aug. 15, 2018 for U.S. Appl. No. 14/465,194, filed Aug. 21, 2014, 64 Pages.
Non-Final Office Action dated Jun. 15, 2020 for U.S. Appl. No. 14/465,194, filed Aug. 21, 2014, 26 Pages.
Non-Final Office Action dated Aug. 17, 2017 for U.S. Appl. No. 14/465,194, filed Aug. 21, 2014, 81 Pages.
Non-Final Office Action dated Dec. 17, 2018 for U.S. Appl. No. 15/799,621, filed Oct. 31, 2017, 10 pages.
Non-Final Office Action dated Jan. 18, 2018 for U.S. Appl. No. 15/799,621, filed Oct. 31, 2017, 10 pages.
Non-Final Office Action dated Jun. 22, 2017 for U.S. Appl. No. 14/461,044, filed Aug. 15, 2014, 21 Pages.
Non-Final Office Action dated Feb. 25, 2021 for U.S. Appl. No. 14/461,044, filed Aug. 15, 2014, 17 Pages.
Non-Final Office Action dated Aug. 28, 2018 for U.S. Appl. No. 16/023,300, filed Jun. 29, 2018, 10 pages.
Non-Final Office Action dated Aug. 28, 2018 for U.S. Appl. No. 16/023,300, filed Jun. 29, 2018, 11 pages.
Non-Final Office Action dated Jun. 28, 2021 for U.S. Appl. No. 16/550,905, filed Aug. 26, 2019, 5 Pages.
Non-Final Office Action received for U.S. Appl. No. 14/155,087 dated Aug. 16, 2016, 28 pages.
Non-Final Office Action received for U.S. Appl. No. 14/155,087 dated Aug. 7, 2017, 28 pages.
Non-Final Office Action received for U.S. Appl. No. 14/155,087 dated Feb. 17, 2016, 26 pages.
Non-Final Office Action received for U.S. Appl. No. 14/155,087 dated Mar. 31, 2015, 22 pages.
Non-Final Office Action received for U.S. Appl. No. 14/155,107 dated Aug. 17, 2016, 37 pages.
Non-Final Office Action received for U.S. Appl. No. 14/155,107 dated Aug. 7, 2017, 34 pages.
Non-Final Office Action received for U.S. Appl. No. 14/155,107 dated Feb. 11, 2016, 42 pages.
Non-Final Office Action received for U.S. Appl. No. 14/155,107 dated Jul. 13, 2018, 45 pages.
Non-Final Office Action received for U.S. Appl. No. 14/155,107 dated Mar. 31, 2015, 26 pages.
Notice of Allowance dated May 1, 2019 for U.S. Appl. No. 16/137,960, filed Sep. 21, 2018, 14 pages.
Notice of Allowance dated Mar. 5, 2019 for U.S. Appl. No. 16/057,573, filed Aug. 7, 2018, 31 Pages.
Notice of Allowance dated Feb. 8, 2019 for U.S. Appl. No. 16/023,276, filed Jun. 29, 2018, 15 pages.
Notice of Allowance dated Mar. 11, 2020 for U.S. Appl. No. 14/465,194, filed Aug. 21, 2014, 29 Pages.
Notice of Allowance dated Jun. 15, 2018 for U.S. Appl. No. 15/799,621, filed Oct. 31, 2017, 27 pages.
Notice of Allowance dated Jul. 18, 2022 for U.S. Appl. No. 16/550,905, filed Aug. 26, 2019, 7 pages.
Notice of Allowance dated Apr. 20, 2022 for U.S. Appl. No. 14/461,044, filed Aug. 15, 2014, 08 pages.
Notice of Allowance dated Sep. 24, 2020 for U.S. Appl. No. 16/292,609, filed Mar. 5, 2019, 20 Pages.
Notice of Allowance dated Mar. 25, 2022 for U.S. Appl. No. 16/550,905, filed Aug. 26, 2018, 7 pages.
Notice of Allowance dated Sep. 25, 2018 for U.S. Appl. No. 14/553,657, filed Nov. 25, 2014, 25 Pages.
Notice of Allowance dated Jan. 28, 2019 for U.S. Appl. No. 16/023,300, filed Jun. 29, 2018, 31 pages.
Notice of Allowance dated Nov. 3, 2022 for U.S. Appl. No. 16/899,843, filed Jun. 12, 2020, 10 pages.
Notice of Allowance dated Mar. 30, 2018 for U.S. Appl. No. 14/539,773, filed Nov. 12, 2014, 17 pages.
Notice of Allowance dated Nov. 30, 2018 for U.S. Appl. No. 15/799,628, filed Oct. 31, 2017, 19 Pages.

(56) References Cited

OTHER PUBLICATIONS

Notice of Allowance received for U.S. Appl. No. 14/155,107 dated Aug. 30, 2019, 16 pages.

Office Action for European Application No. 19806723.3, dated Oct. 27, 2022, 8 pages.

Office Action dated Sep. 28, 2022 for Chinese Application No. 201780059093.7, filed Jul. 25, 2017, 16 pages.

Restriction Requirement dated Aug. 8, 2017 for U.S. Appl. No. 14/553,657, filed Nov. 25, 2014, 7 Pages.

Schowengerdt B.T., et al., "Stereoscopic Retinal Scanning Laser Display With Integrated Focus Cues for Ocular Accommodation," Proceedings of SPIE-IS&T Electronic Imaging, 2004, vol. 5291, pp. 366-376.

Silverman N.L., et al., "58.5L: Late-News Paper: Engineering a Retinal Scanning Laser Display with Integrated Accommodative Depth Cues," SID 03 Digest, 2003, pp. 1538-1541.

Takatsuka Y., et al., "Restriction Projection Display Using Diffractive Optical Element," Tenth International Conference on Intelligent Information Hiding and Multimedia Signal Processing, IEEE, 2014, pp. 403-406.

Urey H., "Diffractive Exit-Pupil Expander for Display Applications," Applied Optics, Nov. 10, 2001, vol. 40 (32), pp. 5840-5851.

Urey H., et al., "Optical Performance Requirements for MEMS-Scanner Based Microdisplays," Conferences on MOEMS and Miniaturized Systems, SPIE, 2000, vol. 4178, pp. 176-185.

Viirre E., et al., "The Virtual Retinal Display: A New Technology for Virtual Reality and Augmented Vision in Medicine," Proceedings of Medicine Meets Virtual Reality, IOS Press and Ohmsha, 1998, pp. 252-257.

Wijk U., et al., "Forearm Amputee's Views of Prosthesis Use and Sensory Feedback," Journal of Hand Therapy, Jul. 2015, vol. 28 (3), pp. 269-278.

Written Opinion for International Application No. PCT/US2014/057029, dated Feb. 24, 2015, 9 Pages.

Office Action dated Feb. 7, 2023 for European Application No. 19810524.9, filed May 28, 2019, 7 pages.

Notice of Allowance dated Dec. 14, 2022 for U.S. Appl. No. 15/882,858, filed Jan. 29, 2018, 10 pages.

Office Action dated Jan. 20, 2023 for Chinese Application No. 201780059093.7, filed Jul. 25, 2017, 16 pages.

SYSTEMS AND METHODS FOR IDENTIFYING BIOLOGICAL STRUCTURES ASSOCIATED WITH NEUROMUSCULAR SOURCE SIGNALS

CROSS-REFERENCE TO RELATED APPLICATIONS

This application claims the benefit under 35 U.S.C. § 119(e) of U.S. Provisional Application Ser. No. 62/574,496, filed Oct. 19, 2017, and entitled "SYSTEMS AND METHODS FOR IDENTIFYING BIOLOGICAL STRUCTURES ASSOCIATED WITH NEUROMUSCULAR SOURCE SIGNALS," the entire contents of which is incorporated by reference herein.

BACKGROUND

Neuromuscular signals arising from the human central nervous system provide information about neural activation that results in the contraction of one or more muscles in the human body. The neuromuscular signals can include traces of neural activation, muscle excitation, muscle contraction, or a combination of the neural activation and the muscle contraction. Some neuromuscular sensors can detect electrical activity produced by skeletal muscle cells upon their activation when positioned on the surface of a human body. Such neuromuscular sensors capture electrical activity as complex and superimposed signals including a combination of electrical activity produced by multiple biological structures. This situation results in the underutilization of neuromuscular sensors for the implementation of reactive systems that can be activated based on electrical activity produced by specific biological structures.

SUMMARY

Some embodiments are directed to a system comprising: a plurality of neuromuscular sensors, each of which is configured to record a time-series of neuromuscular signals from a surface of a user's body; at least one computer hardware processor; and at least one non-transitory computer-readable storage medium storing processor-executable instructions that, when executed by the at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

Some embodiments are directed to a method comprising using at least one computer hardware processor to perform: applying a source separation technique to the time series of neuromuscular signals recorded by a plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

Some embodiments are directed to at least one non-transitory computer-readable storage medium storing processor-executable instructions that, when executed by the at least one computer hardware processor, cause the at least one computer hardware processor to perform: applying a source separation technique to the time series of neuromuscular signals recorded by a plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

Some embodiments are directed to a system comprising: a plurality of neuromuscular sensors, each of which is configured to record a time-series of neuromuscular signals from a surface of a user's body; at least one computer hardware processor; and at least one non-transitory computer-readable storage medium storing processor-executable instructions that, when executed by the at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

Some embodiments are directed to a method, comprising using at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

Some embodiments are directed to at least one non-transitory computer-readable storage medium storing processor-executable instructions that, when executed by at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
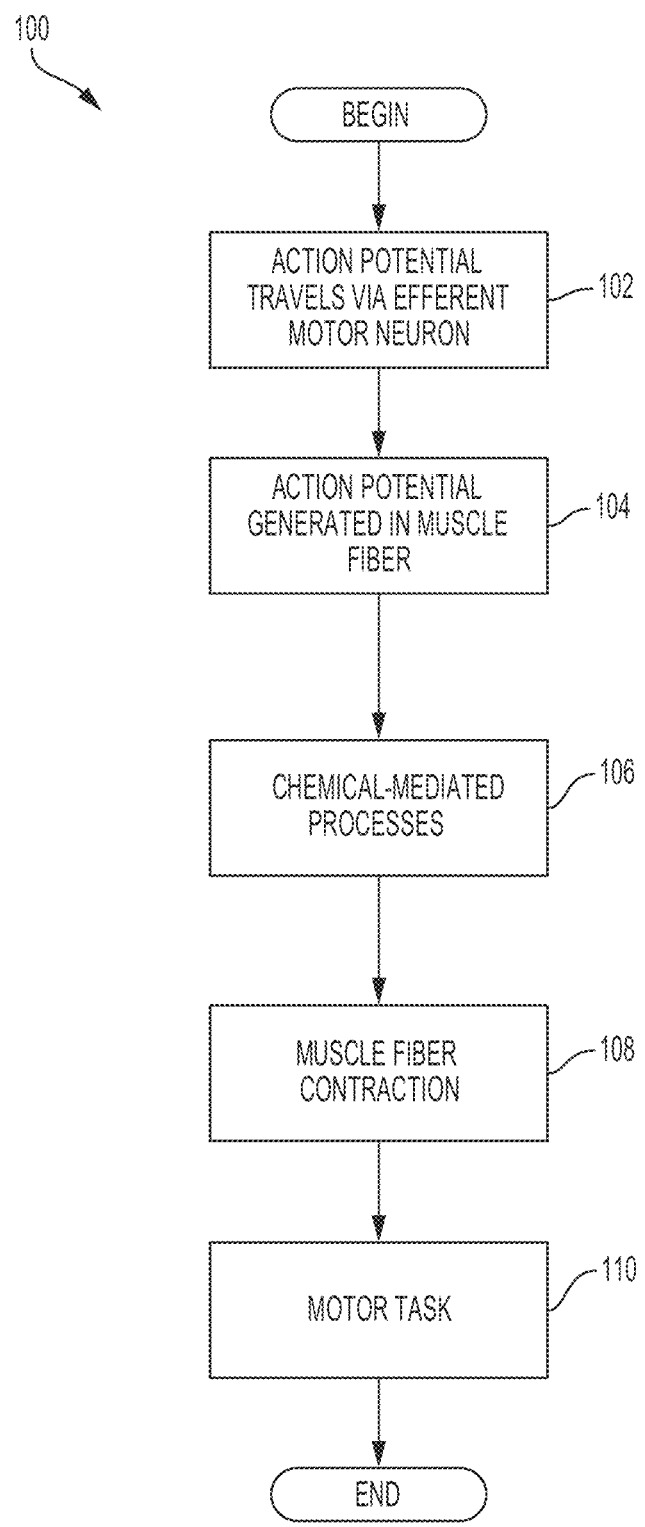
FIG. 1 is a flowchart of a biological process for performing a motor task in accordance with some embodiments of the technology described herein.

The inventors have appreciated that neuromuscular signals detected by neuromuscular sensors depend on a variety of factors including, but not limited to, the precise positions of the neuromuscular sensors on a user, movement of the sensors during recording, and the quality of the contact between the sensors and the users. As these factors often change over time, between uses, and between users, the neuromuscular signals detected by the sensors change as well, which makes it difficult to use neuromuscular signals detected by the sensors for various applications (e.g., controlling physical devices, predicting onset of a motor task, and applications described herein) in a robust and reliable way.

The inventors have also appreciated that recorded neuromuscular signals are formed as a superposition of neuromuscular source signals, each of which may be generated by a corresponding biological structure (e.g., a muscle or muscle group, tendon, motor unit) and that the neuromuscular source signals are less sensitive to the positions, motion, and contact quality of the neuromuscular sensors. Accordingly, the inventors have developed techniques for recovering neuromuscular source signals from recorded neuromuscular signals using source separation and identifying associated biological structures for the neuromuscular source signals such that, with the identification, the neuromuscular source signals may be used for various control and other applications instead of the raw neuromuscular signals themselves. The neuromuscular source signals obtained using the methods described herein exhibit greater stability over time, between different uses by the same user, and between users, than do the raw neuromuscular signals themselves. One important reason for this is anatomical and physiological—the distribution of muscles, motor units, and innervation points/structure is very similar among people.[1]

[1] One exception is the palmaris longus muscle, which is missing in about 14% of the population. The techniques described herein can be used to identify the presence or absence of this muscle in human subjects, which could help further reduce the variability within each of these two groups of people (those with the muscle and those without), and thus aid generalization performance of the methods described herein.

The inventors have appreciated that a need exists for reactive systems that can decompose neuromuscular signals, identify, and selectively capture electrical activity produced by specific biological structures using robust and reliable techniques.

Accordingly, some embodiments involve: (1) recording neuromuscular signals using multiple (e.g., wearable) neuromuscular sensors positioned on a user's body (e.g., EMG, MMG, and SMG sensors); (2) applying a source separation technique (e.g., independent components analysis or non-negative matrix factorization) to the recorded neuromuscular signals to obtain neuromuscular source signals and corresponding mixing information (e.g., a mixing matrix or an unmixing matrix); and (3) identifying, for each of one or more of the neuromuscular source signals, an associated set of one or more biological structures (e.g., one or more muscles, one or more tendons, and/or one or more motor units) whose neuromuscular activity gave rise to the neuromuscular source signal. The identification step may be performed using one or more features derived from the mixing information, the neuromuscular source signals, and/or the recorded neuromuscular signals. Additionally, one or more non-neural features (e.g., experimental design information indicating which biological structures are likely to be most active during an experiment) may be used to perform the identification step, in some embodiments. The biological structures so identified are "device-independent" in that their association with the neuromuscular source signals may be independent of (or at least largely insensitive to) the placement of the sensors and from the types of sensors utilized.

In some embodiments, the above-described acts may be performed in near or real-time, for example, in less than 100 milliseconds, less than 500 milliseconds, less than one second, or less than 5 seconds. In some embodiments, the above-described acts may be performed within a threshold amount of time of the detection of a voltage potential by one or more neuromuscular (e.g., EMG, SMG, or MMG) sensors located on the surface of the body.

Figure 3A:
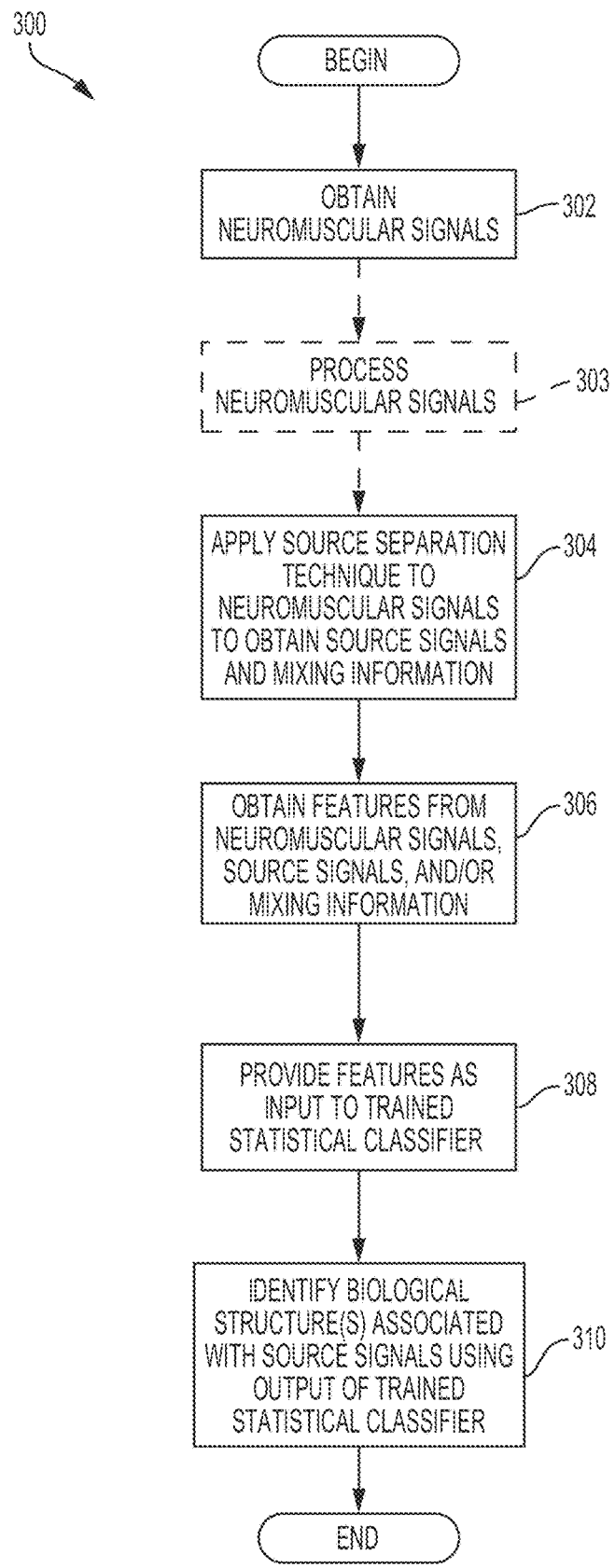
FIG. 3A is a flowchart of an illustrative process for separating recorded neuromuscular signals into neuromuscular source signals and identifying biological structures associated with the neuromuscular source signals, in accordance with some embodiments of the technology described herein.
Figure 3B:
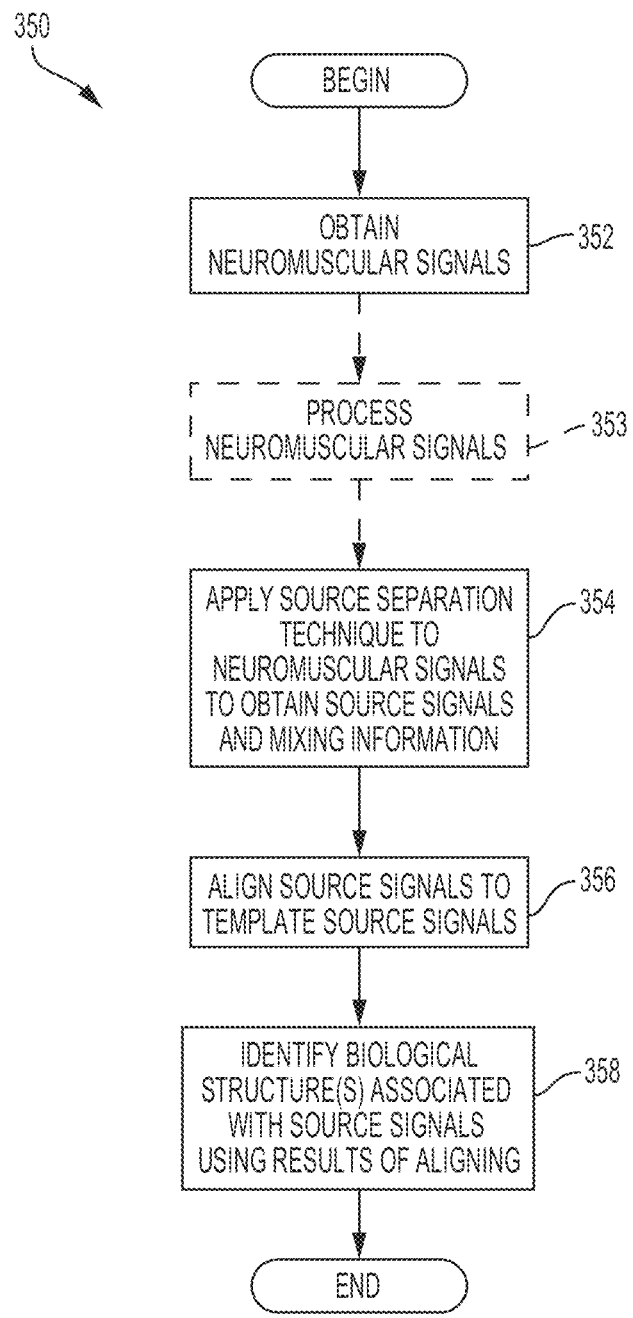
FIG. 3B is a flowchart of another illustrative process for separating recorded neuromuscular signals into neuromuscular source signals and identifying biological structures associated with the neuromuscular source signals, in accordance with some embodiments of the technology described herein.
Figure 3C:
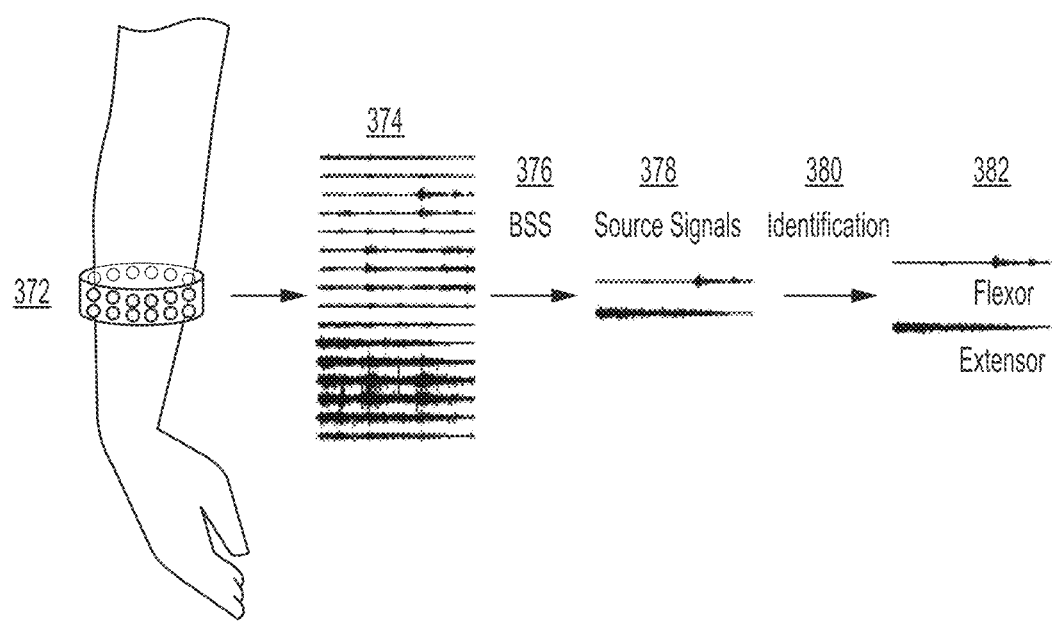
FIG. 3C is a diagram illustrating a process separating recorded neuromuscular signals into two neuromuscular source signals and identifying biological structures associated with the two neuromuscular source signals, in accordance with some embodiments of the technology described herein.

One example of the above-described acts is illustrated in FIG. 3C. As shown in FIG. 3C, neuromuscular signals 374 may be recorded by neuromuscular sensors 372 circumferentially arranged on a wearable wristband worn on a user's arm. A source separation technique 376 may be applied to the neuromuscular signals 374 to generate neuromuscular source signals 378 and corresponding mixing information (not shown). An associated set of one or more biological structures may be identified 380 for each of the two neuromuscular source signals using any of the techniques described herein. As a result, it may be determined, as shown by labels 382, that the first neuromuscular source signal was generated based, at least in part, on neuromuscular activity in at least one flexor muscle and that the second neuromuscular source signal was generated based, at least in part, on neuromuscular activity in at least one extensor muscle.

Associating a set of one or more biological structures with a neuromuscular source signal may provide an indication that the neuromuscular source signal was generated based, at least in part, on neuromuscular activity of the biological structures in the set. The association may be implemented in any suitable way and, for example, by assigning a label to each of the neuromuscular source signals. In some embodiments, a label may identify (directly or indirectly) a set of biological structures so that the constituent structures (e.g., specific muscles, tendons, etc.) may be identified. For example, as shown by labels 382 in FIG. 3C, one source signal may be labeled with a label that indicates the source signal was generated by neuromuscular activity of at least one extensor muscle and another source signal may be labeled with a label that indicates the other source signal was generated by neuromuscular activity of at least one flexor muscle.

In other embodiments, however, a label may not identify a set of biological structures in a way that allows for the constituent muscles, tendons, and/or motor units to be determined. For example, a label may be a number. Rather, in such cases, different labels merely signify that different neuromuscular source signals correspond to different sets of biological structures. In this context, applying the same label to one neuromuscular source signal (e.g., obtained from one set of EMG measurements of a user) and to another neuromuscular source signal (e.g., obtained from another set of EMG measurements of the same user recorded at a later time) indicates that both neuromuscular source signals were generated by neuromuscular activity in the same set of one or more biological structures (even if the constituent structures in the set are partially or fully unknown).

In some embodiments, multiple source signals may be assigned a same label. This may indicate, for example, that the multiple source signals are associated with (e.g., emanate from) the same underlying biological structure. For example, source signals emanating from different muscle fibers may be assigned the same label, which may indicate that the fibers are part of the same muscle. As another example, source signals emanating from different motor units may be assigned the same label, which may indicate that the motor units are part of the same muscle.

In some embodiments, identifying, for each of one or more of the neuromuscular source signals, an associated set of one or more biological structures may be performed by a trained statistical classifier (e.g., a neural network). The trained statistical classifier may receive, as input, one or more features derived from the mixing information, the neuromuscular source signals, and/or the recorded neuromuscular signals. Responsive to the input, the trained statistical classifier may provide as output, for each set i of one or more biological structures source signal and each neuromuscular source signal j, a probability $p_{ij}$ that the jth source signal is to be associated with the ith set of one or more biological structures.

In some embodiments, the trained statistical classifier may be updated or retrained, in real time, by using information obtained from the time-series of neuromuscular signals recorded by the plurality of neuromuscular sensors. For example, the trained statistical classifier may be used to identify biological structures associated with neuromuscular source signals and, subsequently, the neuromuscular source signals, corresponding mixing information, and/or any information derived therefrom may be used to update one or more parameters of the trained statistical classifier. As one example, in some embodiments, classification metrics (e.g., cross entropy, mutual information, etc.) may be used to update one or more parameters of the trained statistical classifier.

In other embodiments, identifying, for each of one or more of the neuromuscular source signals, an associated set of one or more biological structures may be performed by using a set of template source signals each associated with a known set of one or more biological structures. In some embodiments, neuromuscular source signals may be aligned to template neuromuscular source signals and identifying, based on results of the aligning, an associated set of one or more biological structures for each of one or more neuromuscular source signals. For example, if a particular neuromuscular source signal were aligned to a template source signal already associated with a particular group of muscles, then the particular neuromuscular source signal would also be associated with the particular group of muscles.

In some embodiments, aligning neuromuscular source signals to template neuromuscular source signals comprises determining, using a cost function, a distance between first features and second features, the first features obtained from the neuromuscular source signals and/or the corresponding mixing information, the second features obtained from the template neuromuscular source signals and/or corresponding template mixing information.

In some embodiments, the aligning comprises determining, using a cost function, a distance between the corresponding mixing information and the corresponding template mixing information.

In some embodiments, the aligning comprises determining, using a cost function, a distance between the neuromuscular source signals and the template neuromuscular source signals. This may be done in any suitable way and, for example, may be done by: (1) smoothing and/or rectifying the neuromuscular source signals to obtain first processed neuromuscular source signals; (2) smoothing and/or rectifying the template neuromuscular source signals to obtain a second processed neuromuscular source signals; and (3) determining a distance between the first processed neuromuscular source signals and the second processed neuromuscular source signals. In some embodiments, the distance may be computed between the processed neuromuscular source signals directly and/or between features derived therefrom.

In some embodiments, the obtained neuromuscular source signals along with the identification information may be used for any of numerous applications including, but not limited to, prediction of onset of a motor task, control of one or more physical devices, control of one or more virtual representations, and providing a dynamically-updated musculo-skeletal representation comprising a plurality of rigid body segments connected by joints. Any of these tasks may be performed offline or in real-time (e.g., in less than 100 milliseconds, in less than 500 milliseconds, in less than 1 second, or in less than 5 seconds).

For example, in some embodiments, the neuromuscular source signals may be provided as input to a trained statistical model having at least a first input associated with the first set of one or more biological structures and second input associated with the second set of one or more biological structures. This may include: (1) providing the first neuromuscular source signal or data derived from the first neuromuscular source signal to the first input of the trained statistical model (e.g., a recurrent neural network); (2) providing the second neuromuscular source signal or data derived from the second neuromuscular source signal to the second input of the trained statistical model; and (3) controlling at least one device based, at least in part, on output of the trained statistical model.

In some embodiments, controlling of the at least one device includes predicting, based on an output of the trained statistical model, whether an onset of a motor action will occur within a threshold amount of time; and when it is predicted that the onset of the motor action will occur within the threshold amount of time, sending a control signal to the at least one device prior to completion of the motor action by the user.

It should be appreciated that the techniques introduced above and discussed in greater detail below may be implemented in any of numerous ways, as the techniques are not limited to any manner of implementation. Examples of details of implementation are provided herein solely for illustrative purposes. Furthermore, the techniques disclosed herein may be used individually or in any suitable combination, as aspects of the technology described herein are not limited to the use of any particular technique or combination of techniques.

Coordinated movements of skeletal muscles in the human body that collectively result in the performance of a motor task originate with neural signals arising in the central nervous system. The neural signals travel from the central nervous system to muscles via spinal motor neurons, each of which has a body in the spinal cord and axon terminals on one or more muscle fibers. In response to receiving the neural signals, the muscle fibers contract resulting in muscle movement.

FIG. 1 illustrates a flowchart of a biological process 100 for initiating a motor task by the coordinated movement of one or more muscles. In act 102, action potentials are generated in one or more efferent spinal motor neurons. The motor neurons carry the neuronal signal away from the central nervous system and toward skeletal muscles in the periphery. For each motor neuron in which an action potential is generated, the action potential travels along the axon of motor neuron from its body in the spinal cord where the action potential is generated to the axon terminals of the motor neuron that innervate muscle fibers included in skeletal muscles.

A chemical synapse formed at the interface between an axon terminal of a spinal motor neuron and a muscle fiber is called a neuromuscular junction. As an action potential transmitted along the axon of a motor neuron reaches the neuromuscular junction, process 100 proceeds to act 104, where an action potential is generated in the muscle fiber as a result of chemical activity at the neuromuscular junction. In particular, Acetylcholine released by the motor neuron diffuses across the neuromuscular junction and binds with receptors on the surface of the muscle fiber triggering a depolarization of the muscle fiber. Although neuromuscular signals sensed on the body surface generated by individual muscle fibers are small (e.g., less than 100 µV), the collective action of multiple muscle fibers conducting simultaneously results in a detectable voltage potential that may be recorded by neuromuscular (e.g., EMG, SMG, or MMG) sensors located on the surface of the body.

Following generation of an action potential in the muscle fiber, process 100 proceeds to act 106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 100 proceeds to act 108, where the muscle fiber contracts. Muscle fiber contraction is achieved due to the binding of exposed myosin heads with actin filaments in the muscle fiber creating cross-bridge structures. Process 100 then proceeds to act 110, where the collective contraction of muscle fibers in one or more muscles results in the performance of a motor task. The motor task may be a simple task such as a button press, which involves only a few muscles in a finger and/or wrist, a more complex task such as grasping and turning a doorknob involving several muscles of the hand, wrist and arm, or a motor task of any other complexity, as embodiments of the technology described herein are not limited in this respect.

Neural activity, muscle fiber recruitment, muscle contraction and joint movement all precede the completion of a motor task. For example, the chemical-mediated and mechanical processes involved in acts 106 and 108 of process 100 are not instantaneous, but occur over a time period, which may be on the order of hundreds of milliseconds. Accordingly, there is a time delay between when neuromuscular sensors placed on or near the body surface record the generation of action potentials in the muscle fibers at act 104 in process 100 and when the motor task is performed in act 110. In some embodiments, rather than waiting until the intentional action is performed, signals recorded from neuromuscular sensors may be used to predict the motor task to be performed in advance of the task actually being performed by the wearer of the sensors. As discussed herein, in some embodiments, neuromuscular signals recorded by neuromuscular sensors may be processed to obtain neuromuscular source signals and the neuromuscular source signals, rather than the neuromuscular signals themselves, may be used to predict the onset of a motor task to be performed by the wearer of the sensors.

Figure 2:
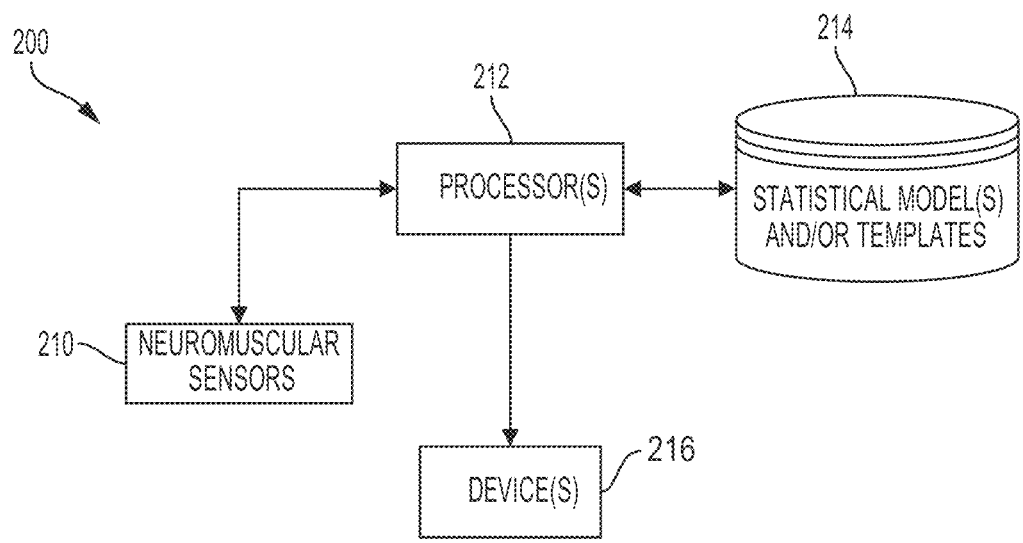
FIG. 2 is a schematic diagram of a computer-based system for separating recorded neuromuscular signals into neuromuscular source signals and identifying biological structures associated with the neuromuscular source signals, in accordance with some embodiments of the technology described herein.

FIG. 2 is a schematic diagram of a computer-based system 200 for separating recorded neuromuscular signals into neuromuscular source signals and identifying biological structures associated with the neuromuscular source signals, in accordance with some embodiments of the technology described herein. System 200 includes a plurality of neuromuscular sensors 210 configured to record signals arising from neuromuscular activity in skeletal muscle of a human body. Neuromuscular sensors 210 may include one or more EMG sensors, one or more MMG sensors, one or more SMG sensors, and/or one or more sensors of any other suitable type that are configured to detect neuromuscular signals.

In some embodiments, EMG sensors include electrodes which detect electric potentials on the surface of the body and hardware processing circuitry that processes the raw EMG signal to perform amplification, filtering (e.g., low pass, high pass, band pass, shaping, narrow band, wide band, temporal etc.), and/or any other suitable type of signal processing (e.g., rectification). Some embodiments employ EMG sensors including hardware signal processing circuitry for processing recorded EMG signals. Other embodiments employ EMG sensors, where at least some of the processing circuitry is performed by one or more circuits in communication with, but not directly integrated with the electrodes that record the signals. In other embodiments, at least some (e.g., all) of the signal processing (e.g., amplification, filtering, rectification, etc.) may be implemented using software rather than by using hardware signal processing circuitry. Thus, signal processing of EMG signals (e.g., amplification, filtering, and rectification) may be performed in hardware only, in software only, or by any combination of hardware and software, as aspects of the technology described herein are not limited in this respect.

In some embodiments, neuromuscular sensors 210 include one or more MMG sensors and/or one or more SMG sensors in addition to or instead of one or more EMG sensors. When used, MMG and SMG sensors may be of any suitable type, as aspects of the technology described herein are not limited in this respect. Some embodiments employ MMG and/or SMG sensors that include hardware signal processing circuitry for performing signal processing (e.g., amplification, filtering, and rectification) on recorded MMG and/or SMG signals. In other embodiments, at least some signal processing of the MMG and/or SMG signals may be performed in software. Thus, signal processing of MMG and/or SMG signals may be performed in hardware only, in software only, or by any suitable combination of hardware and software, as aspects of the technology described herein are not limited in this respect.

In some embodiments, the plurality of neuromuscular sensors 210 includes one or more pairs of neuromuscular sensors arranged as a portion of a wearable device configured to be worn on or around part of a user's body. For example, in one non-limiting example, a plurality of neuromuscular sensors may be arranged circumferentially around an adjustable and/or elastic band such as a wristband or armband configured to be worn around a user's wrist or arm.

Figure 5A:
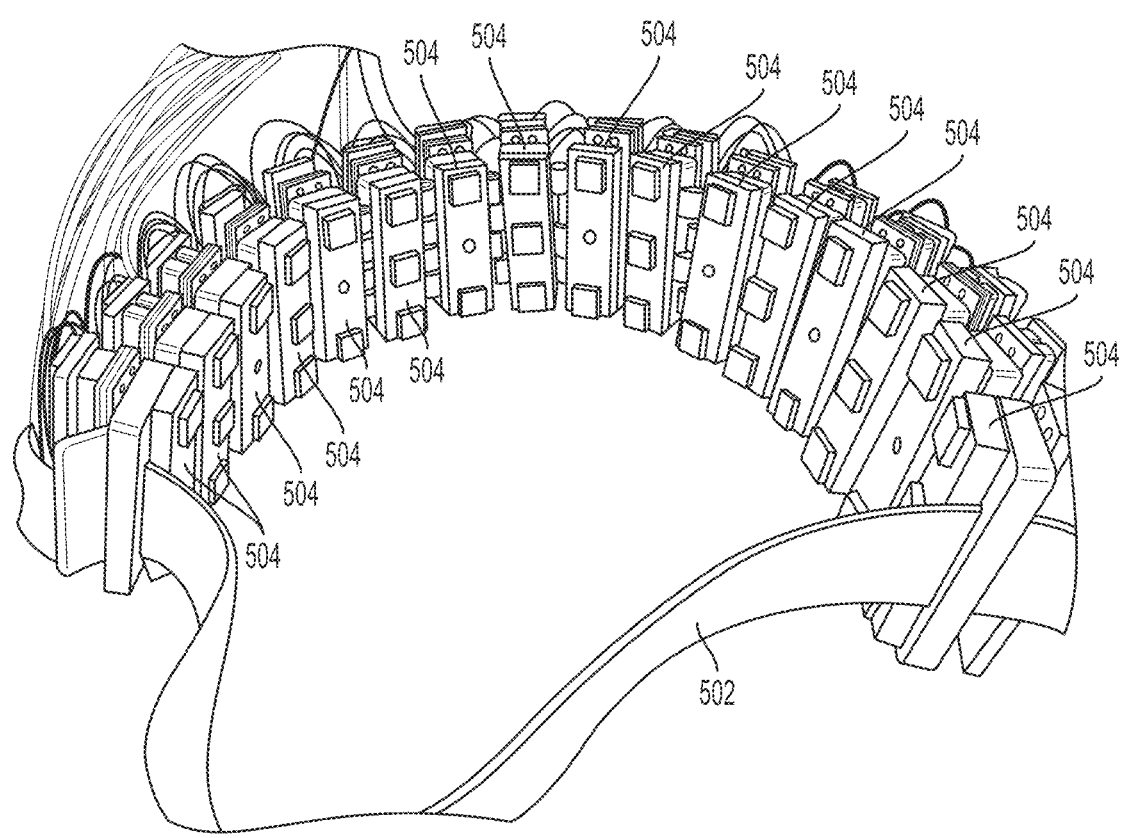
FIG. 5A illustrates a wristband having EMG sensors arranged circumferentially thereon, in accordance with some embodiments of the technology described herein.
Figure 5B:
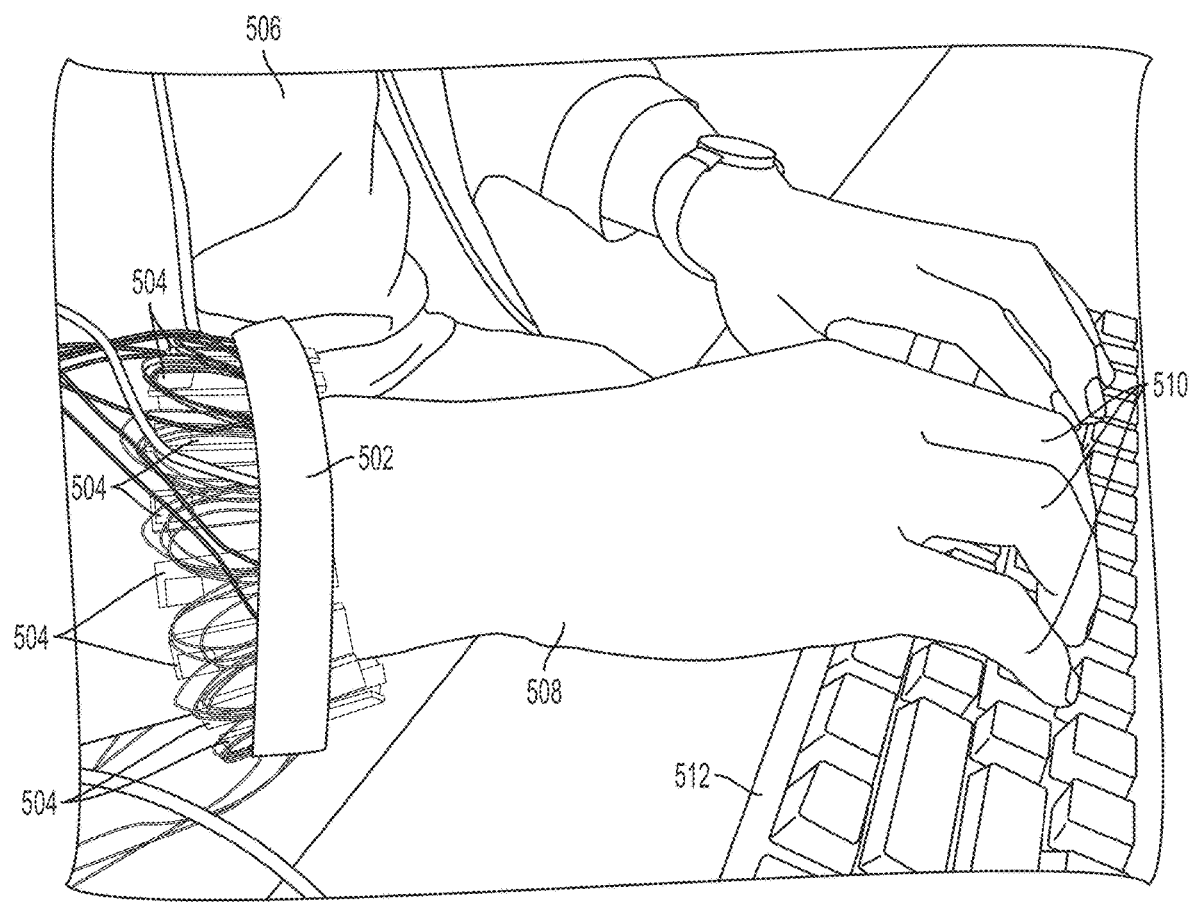
FIG. 5B illustrates a user wearing the wristband of FIG. 5A while typing on a keyboard, in accordance with some embodiments of the technology described herein.

In one illustrative implementation, sixteen (16) neuromuscular sensors are arranged circumferentially around an elastic band configured to be worn around a user's lower arm. For example, FIG. 5A shows neuromuscular sensors 504, which may be EMG sensors in some embodiments, arranged circumferentially around elastic band 502. It should be appreciated that any suitable number of neuromuscular sensors may be used and the particular number and arrangement of neuromuscular sensors used may depend on the particular application for which the wearable device is used. For example, a wearable armband or wristband may be used to predict hand-based motor tasks such as pressing button or moving a joystick, whereas a wearable leg or ankle band may be used to predict foot-based motor tasks such as pressing the gas or brake pedal on a vehicle such as a real or virtual car. For example, as shown in FIG. 5B, a user 506 may be wearing elastic band 502 on hand 508. In this way, neuromuscular sensors 504 may be configured to record EMG signals as a user controls keyboard 512 using fingers 510.

In some embodiments, multiple wearable devices, each having one or more neuromuscular sensors included thereon may be used to predict the onset of complex motor tasks that involve multiple parts of the body.

System 200 also includes one or more computer processors 212 programmed to communicate with sensors 210. For example, neuromuscular signals recorded by neuromuscular sensors 210 may be provided to processor(s) 212 for processing. Processor(s) 212 may be implemented in hardware, firmware, software, or any combination thereof. Additionally, processor(s) 212 may be co-located on the same wearable device as the neuromuscular sensors 210 or may be at least partially located remotely (e.g., processing may occur on one or more network-connected processors).

In some embodiments, processor(s) 212 may be configured to communicate with neuromuscular sensors 210, for example to calibrate the neuromuscular sensors 210 prior to measurement of neuromuscular signals. For example, a wearable device may be positioned in different orientations on or around a part of a user's body and calibration may be performed to determine the orientation of the wearable device and/or to perform any other suitable calibration tasks. Calibration of neuromuscular sensors 210 may be performed in any suitable way, and embodiments are not limited in this respect. For example, in some embodiments, a user may be instructed to perform a particular sequence of movements and the recorded neuromuscular activity may be matched to a template by virtually rotating and/or scaling the signals detected by the sensors (e.g., by the electrodes on EMG sensors). In some embodiments, calibration may involve changing the gain(s) of one or more analog to digital converters (ADCs), for example, in the case that the signals detected by the sensors result in saturation of the ADCs.

Figure 6:
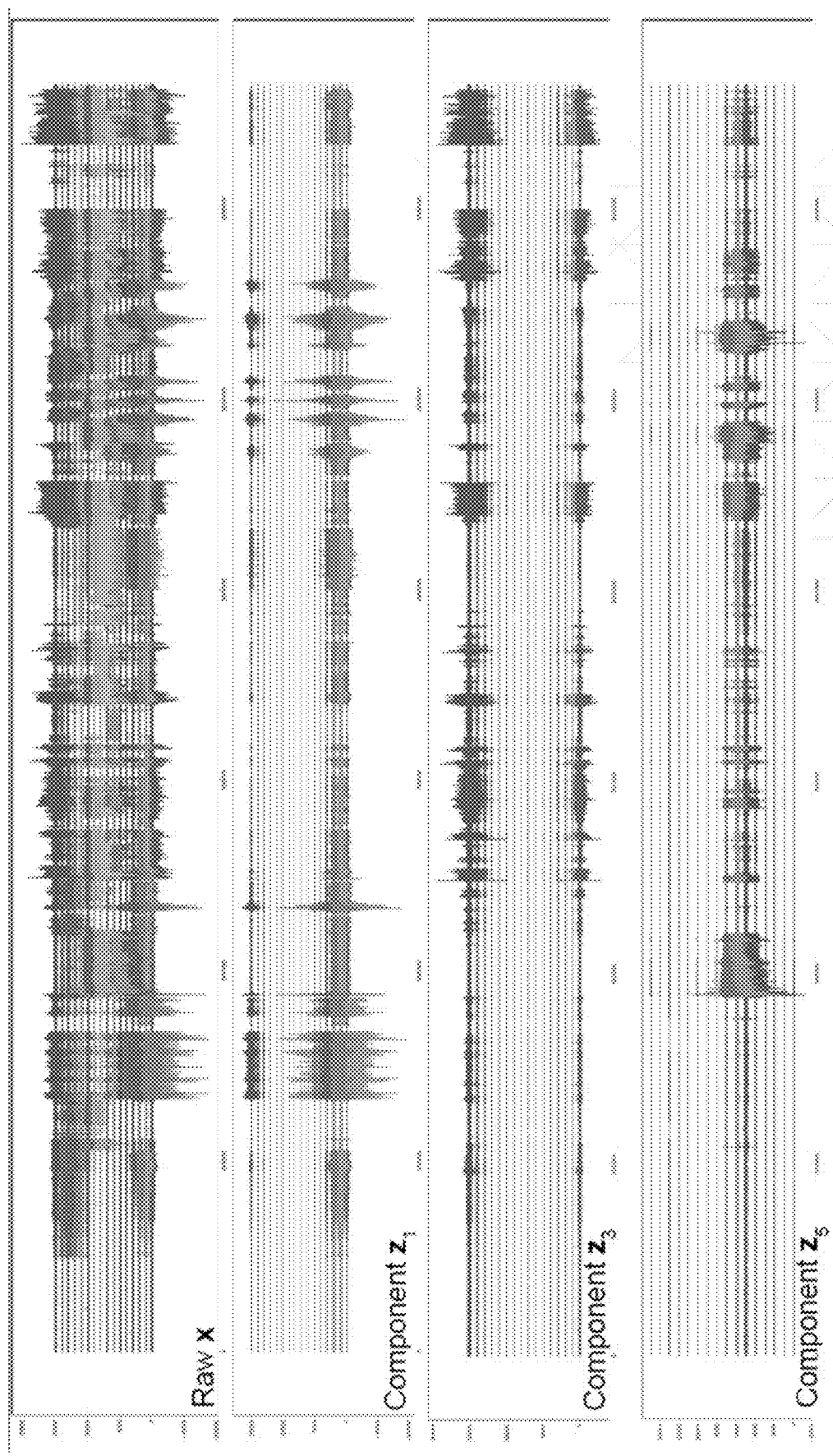
FIG. 6 illustrates neuromuscular signals recorded by multiple neuromuscular sensors and corresponding neuromuscular source signals obtained by using a source separation technique, in accordance with some embodiments of the technology described herein.

In some embodiments, processor(s) 212 may be configured to obtain neuromuscular signals from neuromuscular sensors 210 and process the neuromuscular signals using a source separation technique (e.g., non-negative matrix factorization, independent components analysis, etc.) to obtain neuromuscular source signals and corresponding mixing information. For example, as shown in FIG. 6, EMG signals shown in the top panel may be processed using a source separation technique to obtain neuromuscular source signals including the source signals shown in the second, third, and fourth panels of FIG. 6. The processor(s) 212 may then associate one or more biological structures associated with each of the neuromuscular source signals using neuromuscular signals, neuromuscular source signals, mixing information and/or any information derived therefrom.

In turn, the neuromuscular source signals may be used to predict the onset of motor tasks and/or for any other suitable applications, examples of which are provided herein. For example, in some embodiments, the neuromuscular source signals may be provided as inputs to a trained statistical model (e.g., a neural network, such as a long short term memory neural network or any other suitable machine learning model or machine learning technique) used for prediction of the onset of motor tasks. The trained statistical model may have an input for each of multiple biological structures and the information identifying which neuromuscular source signal is associated with which biological structure can be used to determine which inputs of the trained statistical model should receive which neuromuscular source signals. This is described in more detail herein including with reference to FIG. 4.

System 200 also includes datastore 214 in communication with processor(s) 212. Datastore 214 may include one or more storage devices configured to store information that may be used by processor(s) to identify biological structures associated with the neuromuscular source signals. For example, in some embodiments, datastore 214 may store one or more trained statistical models that may be used to identify biological structures associated with the neuromuscular source signals as described herein, including with reference to FIG. 3A. As another example, in some embodiments, datastore 214 may store templates (obtained from one or more reference sets of neuromuscular signals), which templates may be used to identify biological structures associated with the neuromuscular source signals as described herein, including with reference to FIG. 3B.

Additionally, in some embodiments, datastore 214 may store one or more statistical models used for prediction of the onset of motor tasks in accordance with some embodiments. It should be appreciated that statistical models used for prediction of the onset of motor tasks are different from the statistical models used for identifying biological structures associated with neuromuscular source signals.

System 200 also includes one or more devices 216 configured to be controlled based, at least in part, on processing by processor(s) 212. As discussed herein below, processor(s) 212 may implement a trained statistical model 214 configured to predict the onset of a motor task based, at least in part, on neuromuscular source signals generated from neuromuscular signals recorded by sensors 210 (e.g., EMG sensors, MMG sensors, and SMG sensors), and one or more control signals determined based on the predicted onset of the motor task may be sent to device 216 to control one or more operations of the device with a latency shorter than would be achieved if the control signal was not sent until motor task completion. In some embodiments, device 216 may be controlled with a latency of a duration that is not perceptible, difficult to perceive, or unlikely to be perceived by humans, or with a latency of a duration that is imperceptible to a person with ordinary sensory perception.

Devices 216 may include any device configured to receive control signals through a control interface. Non-limiting examples of devices include consumer electronics devices (e.g., television, smartphone, computer, laptop, telephone, video camera, photo camera, video game system, appliance, etc.), vehicles (e.g., car, marine vessel, manned aircraft, unmanned aircraft, farm machinery, etc.), robots, weapons, or any other device that may receive control signals through one or more control interfaces.

A device 216 may be controlled through any suitable type of control interface. A control interface may be implemented using hardware, software, or any suitable combination thereof. For example, a device 216 may be a video game system which may be controlled through a game controller. As another example, a device 216 may be a computing device, which may be controlled through a keyboard, keypad, and/or a mouse. As another example, a device may be a computing device, which may be touch controlled through a graphical user interface generated by a touch-screen display. As another example, a device may be a vehicle (e.g., a car, an aircraft, a marine vessel, an unmanned aerial vehicle, etc.), which may be controlled through one or more mechanical control devices (e.g., pedals, wheel, joystick, paddles, levers, knobs, etc.).

In some embodiments, system 200 may be trained to predict the onset of one or more motor actions performed by the user. The motor actions may include control actions a user takes with respect to a control interface of a device of devices 216. For example, when the control interface of a device includes one or more buttons, the system 200 may be trained to predict whether a user will press one or more of the buttons within a threshold amount of time. In some embodiments, the system 200 may be trained by recording the neuromuscular signals of one or more users as the user(s) provide input through a control interface of a device and training a statistical model with source signals obtaining by performing source separation on the recorded neuromuscular source signals. After such training, the system 200 may be configured to predict, based on a particular user's neuromuscular source signals derived therefrom, whether the user will perform one or more control actions with respect to the control interface.

In some embodiments, after system 200 is trained to predict, based on a particular user's neuromuscular source signals, whether the user will perform one or more control actions with respect to the control interface of a device, a user may utilize the system 200 to control the device without the control interface. For example, when the system 200 is trained to predict the control actions that the user intends to take with high accuracy (e.g., at least a threshold accuracy), the predictions themselves may be used to control the device.

In some embodiments, a user may utilize a combination of the system 200 and the control interface to control a device. For example, when the system 200 generates a prediction of the control action that the user will take with respect to the control interface and the prediction is generated with at least a threshold amount of confidence and/or within a threshold amount of time of when the predicted action is to take place, the prediction may be used to generate a control signal and the system 200 may control the device. On the other hand, if the prediction is generated with lower than a threshold confidence or is generated too far in advance, the system 200 may be configured to not use such a prediction to control the device. In that case, the user may control the device directly through the control interface.

It should be appreciated that system 200 is not limited to using neuromuscular source signals (and associated labels indicating biological structures) for predicting onset of a motor task. For example, in some embodiments, the neuromuscular source signals may be used for providing a dynamically-updated computerized musculo-skeletal representation comprising a plurality of rigid body segments connected by joints. The neuromuscular source signals may be used (in conjunction with a trained statistical model) to determine musculo-skeletal position information describing a spatial relation (e.g., one or more angles) between two or more connected segments of the rigid body segments in the musculo-skeletal representation, which information, in turn, may be used to update the musculo-skeletal representation. Such techniques for providing a dynamically-updated computerized musculo-skeletal representation may be used to control a visual representation of a character in a virtual reality environment (e.g., when the character is interacting with an object), to control a physical device, and/or various other applications. Techniques for providing a dynamically-updated computerized musculo-skeletal representation using neuromuscular signals is described in U.S. patent application Ser. No. 15/659,072, titled, "METHODS AND APPARATUS FOR PREDICTING MUSCULO-SKELETAL POSITION INFORMATION USING WEARABLE AUTONOMOUS SENSORS", filed on Jul. 25, 2017, which is incorporated by reference in its entirety herein.

In some embodiments, neuromuscular source signals (rather than raw neuromuscular signals themselves) may be used as part of any of the systems described in U.S. patent application Ser. No. 15/659,018, titled "METHODS AND APPARATUS FOR INFERRING USING INTENT BASED ON NEUROMUSCULAR SIGNALS," and filed Jul. 25, 2017, which is incorporated by reference in its entirety herein and/or any systems described in U.S. patent application Ser. No. 15/659,487, titled "ADAPTIVE SYSTEM FOR DERIVING CONTROL SIGNALS FROM MEASUREMENTS OF NEUROMUSCULAR ACTIVITY," and filed on Jul. 25, 2017, which is incorporated by reference in its entirety herein.

As discussed above, some embodiments are directed to identifying biological structures associated with neuromuscular source signals using a trained statistical model. Neuromuscular source signals, obtained by applying a source separation technique to recorded neuromuscular signals, may be provided as inputs to the trained statistical model, and the model may produce output indicative of which biological structures are associated with which neuromuscular source signals. FIG. 3 is a flowchart of an illustrative process 300 for separating recorded neuromuscular signals into neuromuscular source signals and identifying biological structures associated with the neuromuscular source signals, in accordance with some embodiments of the technology described herein.

Process 300 may be executed by any suitable computing device(s), as aspects of the technology described herein are not limited in this respect. For example, process 300 may be executed by processors 212 described with reference to FIG. 2. As another example, one or more acts of process 300 may be executed using one or more servers (e.g., servers part of a cloud computing environment).

Process 300 begins at act 302, where neuromuscular signals are obtained for a user. In some embodiments, the neuromuscular signals may be recorded by neuromuscular sensors positioned on the surface of a user's body as part of process 300. In other embodiments, the neuromuscular signals may have been recorded prior to the performance of process 300 and are accessed (rather than recorded) at act 302.

In some embodiments, the neuromuscular signals may include EMG, MMG, and/or SMG signals recorded for a single user performing one or multiple motor tasks. The user may be instructed to perform a motor task (e.g., pressing one of two buttons) and neuromuscular signals corresponding to the user's neuromuscular activity may be recorded as the user performs the motor task he/she was instructed to perform. The neuromuscular signals may be recorded by any suitable number of neuromuscular sensors located in any suitable location(s) to detect the user's neuromuscular activity that is relevant to the motor task. For example, after a user is instructed to perform a motor task with the fingers of his/her right hand, the neuromuscular signals may be recorded by multiple neuromuscular (e.g., EMG) sensors circumferentially (or otherwise) arranged around the user's lower right arm. As another example, after a user is instructed to perform a motor task with his/her leg (e.g., to push one of two pedals, for example, either a gas or brake pedal in a car), the neuromuscular signals may be recorded by multiple neuromuscular sensors circumferentially (or otherwise) arranged around the user's leg.

In some embodiments, the neuromuscular signals may be recorded at multiple time points as a user performs a motor task. As a result, the recorded neuromuscular signals may include neuromuscular data obtained by multiple neuromuscular sensors at each of multiple time points. Assuming that n neuromuscular sensors are arranged to simultaneously measure the user's neuromuscular activity during performance of the motor task, the recorded neuromuscular signals for the user may comprise a time series of K n-dimensional vectors $\{x_k | 1 \leq k \leq K\}$ at time points $t_1, t_2, \ldots, t_K$.

Next, process 300 proceeds to act 303, where the neuromuscular signals are preprocessed. In some embodiments, the neuromuscular signals obtained at act 302 may be pre-processed using amplification, filtering, rectification, and/or any other suitable type of signal processing technique. In some embodiments, the filtering may comprise temporal filtering implemented using convolution operations and/or equivalent operations in the frequency domain (e.g., after the application of a discrete Fourier transform). As indicated by the dashed lines in FIG. 3A, act 303 is optional and may be omitted, in some embodiments.

Next, process 300 proceeds to act 304 where a source separation technique is applied to the neuromuscular signals obtained at act 302 to obtain neuromuscular source signals and corresponding mixing information. The source separation technique applied at act 304 may be a blind source separation technique. In some embodiments, independent component analysis (ICA) may be applied to the neuromuscular signals obtained at act 302 to obtain neuromuscular source signals and corresponding mixing information. Independent component analysis may be implemented using any of numerous techniques including, but not limited to, projection pursuit, maximum likelihood estimation, and information maximization.

As another example, in some embodiments, non-negative matrix factorization (NNMF) may be applied to the neuromuscular signals obtained at act 302 to obtain neuromuscular source signals and corresponding mixing information. In some embodiments, the non-negative matrix factorization may be implemented using any of numerous approximate techniques such as, for example, the multiplicative update rule method, alternative non-negative least squares, regularized least squares, gradient descent methods, the active set method, the optimal gradient method, the block principal pivoting method, and/or any other suitable technique. In some embodiments, non-negative matrix factorization may be implemented using an algorithm that's provably exact (rather than approximate) provided certain constraints are met by the matrix encoding the neuromuscular signals obtained at act 302 and, optionally, pre-processed at act 303.

It should be appreciated that while, in some embodiments, ICA, NNMF or variants thereof may be used to perform source separation, different source separation and/or deconvolution techniques may be applied in other embodiments, as aspects of the technology described herein are not limited in this respect. For example, principal component analysis (PCA), stationary subspace analysis, or singular value decomposition may be used in other embodiments. As another example, beamforming, convolutive kernel compensation, common spatial pattern (CSM) method, stationary subspace analysis, and/or dependent component analysis may be used in some embodiments. It should also be appreciated that the source separation technique applied at act 302 is not limited to being a blind source separation technique. For example, informative priors or other information may be used in some embodiments.

As described herein, a source separation technique may be applied to the obtained and, optionally, pre-processed neuromuscular signals (mixed neuromuscular signals) to obtain neuromuscular source signals (unmixed neuromuscular signals) and corresponding mixing information. In some embodiments, the mixing information may indicate how to combine the neuromuscular source signals to obtain the mixed neuromuscular source signals or an approximation to the mixed neuromuscular source signals. In some embodiments, the mixing information may specify a mixing transformation that, when applied to the neuromuscular source signals, generates the mixed neuromuscular signals or an approximation thereto. In some embodiments, the transformation may be embodied in a matrix, which may be referred to as a mixing matrix.

For example, in some embodiments, m mixed neuromuscular signals each having n measurements may be organized in an m×n matrix A. Such signals may be obtained by each of m neuromuscular sensors recording a time series of n measurements. Applying a source separation technique to the data in matrix A, to unmix the data into k sources, may generate an m×k matrix B and a k×n matrix C. In this example, the matrix C includes the k neuromuscular source signals, each of which consists of n measurements. The neuromuscular source signals are rows of the matrix C. In this example, the matrix B is the mixing matrix indicating how to combine the source signals to obtain the mixed neuromuscular signals or an approximation thereto. A row i ($1 \leq i \leq m$) of the matrix B indicates the relative contributions (sometimes called "weights" or "loadings") of each of the k neuromuscular source signals toward the unmixed neuromuscular source signal recorded by the ith neuromuscular sensor. The loadings capture the degree of influence that a particular source signal (which is generated through action of a particular muscle, muscle group, etc.) has on the signal recorded by a particular neuromuscular sensor.

In some embodiments, the mixing information may indicate how to separate the mixed neuromuscular signals to obtain the unmixed neuromuscular source signals. In some embodiments, the mixing information may specify an unmixing transformation that, when applied to the mixed neuromuscular signals, generates the unmixed neuromuscular source signals or an approximation thereto. In some embodiments, the transformation may be embodied in a matrix, which may be referred to as an unmixing matrix.

As described herein, a source separation technique may be applied to N neuromuscular source signals to obtain k neuromuscular source signals. In some embodiments, the number of sources k may be determined in advance prior to performing process 300. The number of sources may be determined in any suitable way. For example, the number of sources may be selected such that applying the mixing transformation to that number of sources generates a good approximation (e.g., via an autoencoder, via a generative statistical model for each value of k) of the mixed neuromuscular signals recorded by the neuromuscular sensors in a training set. As another example, the number of sources may be determined by considering where the neuromuscular sensor(s) are to be placed and determining, from the anatomy and the placement, how many muscles would be accessible to the sensors. The number of sources may be set based on (e.g., equal to, to be less than) the number of accessible muscles. As another example, the number of sources may be selected as the number that results in a fitted model with the highest likelihood of held out validation data. As yet another example, the number of source may be selected as large as possible (e.g., all of the independent components from ICA), but then discarding sources that do not meet one or more quality control metrics (e.g., expected temporal autocorrelation, spatial distribution of weights on electrodes conforms to expectations given sensor positioning, etc.).

Next, process 300 proceeds to act 306, where one or more features are obtained from: (1) the mixed neuromuscular signals obtained at act 302 and, optionally, processed at act 303; (2) the neuromuscular source signals obtained at act 304; and/or (3) the mixing information obtained at act 304. The features obtained at act 306 are then applied as inputs to a trained statistical classifier at act 308. The output of the trained statistical classifier is obtained at act 310 and used to associate one or more biological structures (examples of which are provided herein) with the neuromuscular source signals.

Any suitable features may be obtained at act 306. For example, in some embodiments, the features obtained at act 306 may include at least some information specifying the mixing transformation (e.g., the mixing matrix) and/or the unmixing transformation (e.g., the unmixing matrix). As one specific example, the features obtained at act 306 may include an unmixing matrix. As another example, the features obtained at act 306 may include at least a subset (e.g., all) of the mixed neuromuscular signals and/or statistics derived therefrom. As yet another example, the features obtained at act 306 may include at least a subset (e.g., all) of the unmixed neuromuscular source signals and/or statistics derived therefrom. In some embodiments, the features obtained at act 306 may include any combination of the foregoing features. For example, in some embodiments, the features obtained at act 306 may include the unmixing matrix, statistics computed from the mixed neuromuscular signals (e.g., correlations between raw signals, correlations between smoothed and/or rectified signals, etc.), and statistics computed from the unmixed neuromuscular source signals (e.g., correlations between raw signals, correlations between smoothed and/or rectified signals, etc.).

The features obtained at act 306 are provided as inputs to a trained statistical classifier at act 308. In some embodiments, the trained statistical classifier may be a neural network. The neural network may be a multi-layer neural network, a feedforward neural network, a convolutional neural network, or a recurrent neural network (e.g., a long short-term memory neural network, a fully recurrent neural network, a recursive neural network, a Hopfield neural network, an associative memory neural network, an Elman neural network, a Jordan neural network, an echo state neural network, a second order recurrent neural network, and/or any other suitable type of recurrent neural network).

In some embodiments, where the trained statistical model is a neural network, the output layer of the neural network may be configured to output a matrix of numbers $O_{ij}$, with the entry (i,j) in the matrix indicating a likelihood or probability that the jth neuromuscular source signal is to be associated with biological structure i. In such embodiments, each entry in the matrix $O_{ij}$ may be computed by a corresponding output node in the output layer of the neural network. As a result, the output nodes may be grouped into rows and columns based on which entries in the output matrix they produce.

In some embodiments, the rows of the output matrix are normalized to 1 and represent probabilities. In such embodiments, the neural network may include a softmax transformation along rows of output nodes. In other embodiments, the columns of the output matrix may be normalized to 1 and represent probabilities. In such embodiments, the neural network may include a softmax transformation along columns of output nodes.

It should be appreciated, however, that the trained statistical classifier is not limited to being a neural network and may be any other suitable trained statistical classifier configured to generate, for each neuromuscular source signal, a plurality of likelihoods or probabilities that the neuromuscular source signal is to be associated with a respective plurality of biological structures. For example, in some embodiments, the trained statistical classifier may be a graphical model, a Gaussian mixture model, a support vector machine, a regression-based classifier, a decision tree classifier and/or any other suitable classifier, as aspects of the technology described herein are not limited in this respect.

Regardless of the type of trained statistical classifier employed at act 308, the output of the trained statistical classifier may be used, at act 310, to associate each of the neuromuscular source signals with a corresponding biological structure or structures. In some embodiments, the probabilities output by the trained statistical classifier may be used to assign or label each neuromuscular source signal with a corresponding biological structure. For example, biological structures may be assigned to the neuromuscular source signals in a way that maximizes the product of the estimated probabilities that the assignment (ordering) is correct. If the number of source signals is too large to check all possibilities, an approximate (e.g., greedy) algorithm may be used to assign biological structures to source signals.

The statistical classifier used in process 300 as part of act 308 may be trained prior to the execution of process 300 using training data. The training data may be obtained by: (1) obtaining a large number of neuromuscular signals (e.g., making recordings, rescaling existing recordings, permuting recordings made by a set of electrodes, for example, by rotating the electrodes, etc.); (2) applying a source separation technique to the neuromuscular signals (e.g., the source separation technique described with reference to act 304) to obtain neuromuscular source signals and corresponding mixing information; (3) extracting input features use for training the statistical classifier (e.g., extracting the same features as described with reference to act 306); and (4) determining for each of the neuromuscular source signals an associated biological structure. This last step of labeling neuromuscular source signals with corresponding biological structures may be performed by hand, using a biophysical model of the human anatomy, using any of the template matching techniques described herein with reference to FIG. 3B, or in any other suitable way. The features and labels so obtained may be used to train the statistical classifier. In the case of a neural network, the features and labels may be used to estimate the weights of the neural network (e.g., using gradient descent, backpropagation, etc.).

It should be appreciated that process 300 is illustrative and that there are variations. For example, in some embodiments, one or more features not derived from neuromuscular signals obtained at act 302 may be used to identify the biological structure(s) associated with the source signals. For example, in some embodiments, information about the design of the experiment during which the neuromuscular source signals are obtained may be used. For example, one or more features indicating which biological structures are likely to be most active during the experiment may be used as inputs (or parameters) to the trained statistical classifier.

As another example, in some embodiments, output of the trained statistical classifier not only may indicate a biological structure to associated with a neuromuscular source signal, but also may provide information about the biological structure. For example, when the biological structure includes a motor unit, the information may include information about features associated with the motor unit (e.g., frequency, count, or other time-series features corresponding to the motor unit). As another example, information about a muscle's time-dependent activity may be obtained. As yet another example, information indicating the number of distinct observable motor units in a muscle may be obtained.

It should be appreciated that the number k of neuromuscular source signals in the case of illustrative process 300 may change over time, in some embodiments. For example, as a greater number of neuromuscular signals is gathered, the techniques described herein may be able to detect the presence of more biological structures with higher accuracy. In such instances, the number of neuromuscular source signals may be increased. Conversely, the number of neuromuscular source signals may decrease if the neuromuscular signals gathered become unreliable or otherwise corrupted (e.g., when a sensor becomes damaged). Such functionality may be implemented in any suitable way. In some embodiments, for example, multiple trained statistical classifiers (e.g., with each one configured to receive features generated from a respective number k of neuromuscular source signals) may be maintained and output from only the trained classifier corresponding to the "current" value of k may be used.

FIG. 3B is a flowchart of an illustrative process 350 for separating recorded neuromuscular signals into neuromuscular source signals and identifying biological structures associated with the neuromuscular source signals, in accordance with some embodiments of the technology described herein.

Process 350 may be executed by any suitable computing device(s), as aspects of the technology described herein are not limited in this respect. For example, process 350 may be executed by processors 212 described with reference to FIG. 2. As another example, one or more acts of process 350 may be executed using one or more servers (e.g., servers part of a cloud computing environment).

Process 350 begins at acts 352 and 353 where neuromuscular signals are obtained and processed. Acts 352 and 353 may be performed in any suitable way including in any of the ways described herein with reference to acts 302 and 303 of process 300.

Next, process 350 proceeds to act 354, where a source separation technique is applied to neuromuscular signals obtained at act 352 (and optionally processed at act 353) to obtain neuromuscular source signals and corresponding mixing information. Act 354 may be performed in any suitable way including in any of the ways described herein with reference to act 304 of process 300.

Next, process 350 proceeds to act 356, where the neuromuscular source signals obtained at act 354 are aligned to template neuromuscular source signals. The template source signals may be obtained in any suitable way and, for example, may be obtained by applying the same source separation technique as applied to source signals to a reference dataset. The template source signals may be labeled in any suitable way. In some embodiments, the template source signals may be simply numbered (e.g., 1, 2, 3., etc.) or associated with any suitable identifiers. In some embodiments, identifiers assigned to the template source signals may have anatomical significance. Such anatomically-meaningful labels may be obtained by: (1) using invasive intramuscular EMG recordings in which electrodes are inserted into identified muscles; (2) using auxiliary information (e.g., motion tracking, prior knowledge of which muscles are involved in which movements, etc.); and/or in any other suitable way.

In some embodiments, the neuromuscular source signals may be aligned to template neuromuscular source signals by using a cost function. The cost function may reflect the degree of alignment between neuromuscular source signals and template neuromuscular source signals. For example, in some embodiments, a cost function may be used to compute the distance between a first features and second features. The first features may be derived from the neuromuscular source signals obtained at act 354, the corresponding mixing information, and/or the unmixed neuromuscular signals from which the neuromuscular source signals were obtained. The second features may be derived from the template neuromuscular source signals, the corresponding template mixing information, and/or the unmixed template neuromuscular signals from which the template neuromuscular source signals were obtained. Thus, the value of the cost function may depend on any of the above-described data. For example, in some embodiments, the cost function may depend on the raw neuromuscular signals, the unmixing matrix, and/or the unmixed source signals.

For example, in some embodiments, the aligning may be performed by using a cost function that depends on the mixing information for the neuromuscular source signals and the template mixing information for the template neuromuscular source signals. One example of such a cost function is given by:

$$C(A) = \min_i \| rot(A,i) - A_t \|^2,$$

where the matrix A is an unmixing matrix obtained at act 354, $A_t$ is the unmixing matrix for the template neuromuscular signals, rot( ) is the rotation operator cycling columns of the matrix A, and $\| \; \|$ denotes the Euclidean norm. Optimizing (e.g., minimizing) this cost function over possible rotations of the electrodes may be performed by cycling the columns of the matrix A. The minimizing (or otherwise optimizing) rotation provides an alignment between the neuromuscular source signals and the corresponding template source signals.

In some embodiments, the above cost function may additionally or alternatively include a term that relates the covariances of smoothed and rectified versions of the neuromuscular source signals and template neuromuscular source signals (e.g., $\| Cov(S) - Cov(S_t) \|^2$) where S denotes the set of neuromuscular source signals, $S_t$ denotes the set of template neuromuscular source signals, and Cov( ) is the covariance operator. In some embodiments, the cost function could also involve a term based on activity patterns during a calibration routine. The cost function could take the form of a negative likelihood in the case of a probabilistic model.

In some embodiments, other second-order statistical quantities may be employed instead of a covariance. For example, in some embodiments, cross-correlation, time-lagged covariances, cross-spectral densities, and/or any other quantities derived from such statistical quantities may be employed.

In some embodiments, minimizing the cost function may be computationally expensive since the number of possible alignments increases exponentially with the number of source signals to align. In such instances, approximate techniques for minimizing the cost function may be utilized including, for example, stochastic minimization methods such as Gibbs sampling or simulated annealing.

Next, process 350 proceeds to act 358, where each of one or of the neuromuscular source signals is associated with a corresponding set of one or more biological structures based on results of the alignment. For example, if a particular neuromuscular source signal were aligned to a template source signal already associated with a particular group of muscles, then the particular neuromuscular source signal would also be associated with the particular group of muscles.

In some embodiments, an association between a neuromuscular source signal and a corresponding biological structure may be associated with a confidence measure (e.g., a value indicating the confidence in the accuracy of the association). Associations of different neuromuscular signals to respective biological structures may have different confidences. For example, a first neuromuscular source signal may be associated with a first biological structure and that association may have a first confidence, a second neuromuscular source signal may be associated with a second biological structure and that association may have a second confidence, and the first and second confidences may be different from one another.

It should be appreciated that process 400 is illustrative and that there are variations. For example, in some embodiments, one or more features not derived from neuromuscular signals obtained at act 402 may be used to identify the biological structure(s) associated with the source signals. For example, in some embodiments, information about the design of the experiment during which the neuromuscular source signals are obtained may be used. For example, one or more features indicating which biological structures are likely to be most active during the experiment may be used to weight the scores for alignments performed at act 358 or in any other way.

It should be appreciated that, in some embodiments, techniques other than those described with reference to FIG. 3A and FIG. 3B may be used to identify biological structures associated with source signals. As one non-limiting example, in the case when there are two source signals obtained from the recorded neuromuscular signals, the identification may be performed based on asymmetries in the corresponding mixing information.

As a simple non-limiting example, applying non-negative matrix factorization to neuromuscular signals obtained (by EMG sensors disposed circumferentially on a wristband) when a user performed wrist flexion and extension results in two neuromuscular source signals and associated mixing information that includes the loading coefficients. The loading coefficients may be used to identify one source signal with one or more flexor muscles and another source signal with one or more extensor muscles based on rotational asymmetry of the loading coefficients. In particular, one source signal has larger loading coefficients (due to higher levels of activity) than the other, and spatially the peaks of the two components were not offset 180 degrees from each other, but rather were closer together such that, if one were to go around the electrode clockwise, one would encounter a large gap, then the peak of component A, then a small gap, then the peak of component B. In such instances, the source signals may be identified by: (1) identifying the peaks of the loading coefficients for each of the two neuromuscular source signals; and (2) label the components as A and B such that going clockwise, there is a smaller gap from the peak of A to the peak of B while there is a larger gap from the peak of B to the peak of A. As another example, the components may be oriented based on the spatial peak around the electrodes and then aligned relative to the peak activity when a certain gesture is involved.

Figure 4:
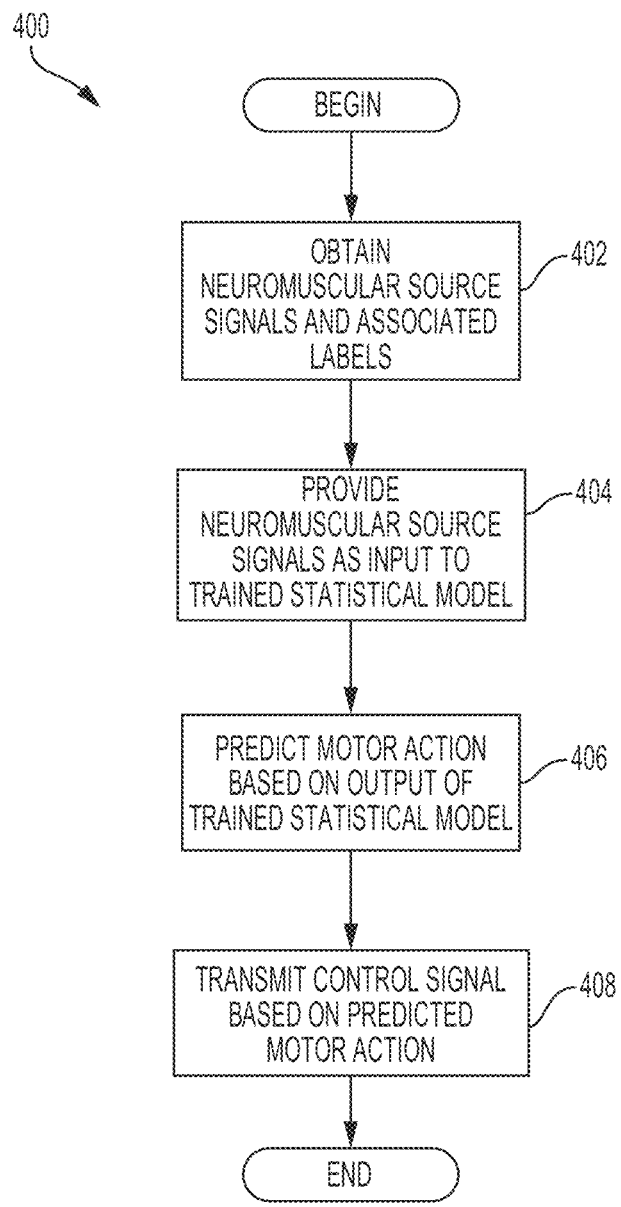
FIG. 4 is a flowchart of an illustrative process for using a trained statistical model to predict the onset of one or more motor tasks using neuromuscular source signals obtained using the process described with reference to FIG. 3A or with reference to FIG. 3B, in accordance with some embodiments of the technology described herein.

FIG. 4 is a flowchart of an illustrative process 400 for using a trained statistical model to predict the onset of one or more motor tasks using neuromuscular source signals obtained using either of the processes described with reference to FIG. 3A and FIG. 3B, in accordance with some embodiments of the technology described herein. Process 400 may be used to predict the onset of a motor task based on recorded neuromuscular signals with short latency. In some embodiments, recorded neuromuscular signals may be unmixed using a source separation technique (e.g., a blind source separation technique) to generate neuromuscular source signals and the source signals may be labeled as being associated with respective biological structures, as described with reference to FIGS. 3A and 3B. In turn, the neuromuscular source signals may be provided as inputs to a trained statistical model (in the appropriate order implied by the labeling—as the trained statistical model will have certain inputs that correspond to particular biological structures) that can predict the onset of a task.

As a non-limiting example, process 400 may be used to predict, based on a plurality of neuromuscular source signals, a likelihood that a button will be pressed prior to the user actually pressing the button. In some embodiments the prediction can be made 10 milliseconds prior to the action being performed, in other embodiments the prediction can be made 50 milliseconds, 100 milliseconds, 200 milliseconds, or 250 milliseconds prior to the task being performed. The prediction may be made 50-100 milliseconds, 100-200 milliseconds, or 200-300 milliseconds prior to the task being performed in some embodiments. The prediction of a user's intention to perform a motor task in accordance with some embodiments can be used to control devices at short latency, as discussed in more detail below.

Process 400 begins at act 402 where neuromuscular source signals and associated labels are obtained. The labels may indicate which biological structures the source signals are associated with. The labels need not have any particular nomenclature. In some embodiments, the labels may specify a numerical ordering. For example, the first source signal may be labeled #3, the second source signal may be labeled #1, the third source signal may be labeled #2, etc. This ordering may indicate which biological structures have been associated with which source signals. For instance, in the above example, the first source signal has been identified as being generated by neuromuscular activity of biological structure #3, the second source signal has been identified as being generated by neuromuscular activity of biological structure #1, and the third source signal has been identified as being generated by neuromuscular activity of biological structure #2.

In some embodiments, the neuromuscular source signals and respective labels identifying associated biological structures may be obtained using a trained statistical classifier, as described herein including with reference to FIG. 3A. In other embodiments, the neuromuscular source signals and respective labels identifying associated biological structures may be obtained using template-based methods, as described herein including with reference to FIG. 3B.

Next, process 400 proceeds to act 404 where the neuromuscular source signals are provided as inputs to a trained statistical model for predicting the onset of a motor task. The trained statistical model may be of any suitable type, including of any suitable type described in U.S. patent application Ser. No. 15/659,018, titled "METHODS AND APPARATUS FOR INFERRING USING INTENT BASED ON NEUROMUSCULAR SIGNALS," and filed Jul. 25, 2017, which is incorporated by reference in its entirety herein. For example, the trained statistical model may be a long short-term memory recurrent neural network.

The trained statistical model may have a plurality of inputs, each of the inputs being for source signals generated by neuromuscular activity by a respective biological structure or information derived from such source signals. As such, the labels of the neuromuscular source signals provide an indication as to which inputs of the trained statistical model are to receive which neuromuscular source signals.

For example, a trained statistical model having two sets of inputs—one set of one or more inputs for neuromuscular source signals generated by neuromuscular activity of the flexor muscle (and/or information derived therefrom) and another set of one or more inputs for neuromuscular source signals generated by neuromuscular activity of the extensor muscle (and/or information derived therefrom). Neuromuscular signals collected by a group of (e.g., 16) EMG sensors may be processed to obtain 2 neuromuscular source signals. The first source signal may be labeled as #2, indicating that the first source signal is generated as a result of neuromuscular activity by the extensor muscle. The second source signal may be labeled as #1, indicating that the second source signal is generated as a result of neuromuscular activity by the flexor muscle. As a result, the second source signal (and/or any information derived therefrom) may be applied as inputs to the first set of inputs of the trained statistical model. The first source signal (and/or any information derived therefrom) may be applied as inputs to the second set of inputs of the trained statistical model.

After the trained statistical model receives the neuromuscular source signals as inputs, process 400 proceeds to act 406, where the probability of one or more motor actions occurring within a particular time threshold is output from the trained statistical model. In some embodiments, the output of the trained statistical model may be a set of probability values (e.g., 0.8, 0.15, and 0.05) indicating the respective probabilities that the user will perform a respective action within a threshold amount of time in the future. The prediction of whether and/or what motor action the user will perform within the threshold amount of time may be determined by comparing the output set of probability values with an operating threshold set for a particular task or application.

After a motor action is predicted in act 406, process 400 proceeds to act 408, where a control signal is transmitted to a device based, at least in part, on the predicted motor action. Preferably the control signal is transmitted to the device as soon as possible following the prediction in act 406 to increase the amount of time between when the control signal based on the prediction is sent to the device and the time when the control signal would have been sent had the control signal been sent in response to completion of the motor action.

Various aspects of the technology described herein may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of some embodiments of the technology described herein comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments. The computer-readable storage medium can be transportable such that the program stored thereon can be loaded onto any computer resource to implement the aspects of the technology discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology described herein.

Figure 7:
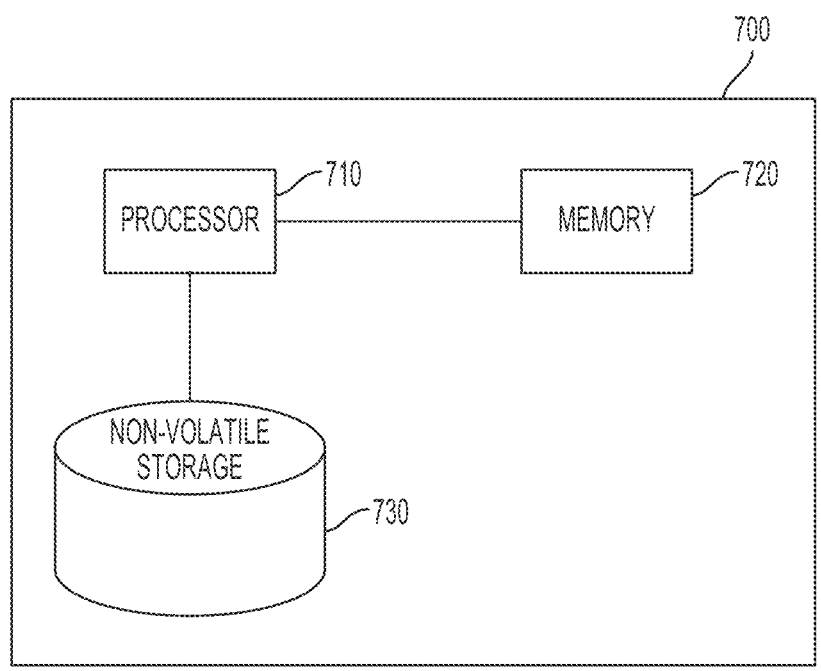
FIG. 7 is a diagram of an illustrative computer system that may be used in implementing some embodiments of the technology described herein.

An illustrative implementation of a computer system 700 that may be used in connection with any of the embodiments of the disclosure provided herein is shown in FIG. 7. For example, the processes described with reference to FIGS. 3A and 3B may be implemented on and/or using computer system 700. The computer system 700 may include one or more processors 710 and one or more articles of manufacture that comprise non-transitory computer-readable storage media (e.g., memory 720 and one or more non-volatile storage media 730). The processor 710 may control writing data to and reading data from the memory 720 and the non-volatile storage device 730 in any suitable manner, as the aspects of the disclosure provided herein are not limited in this respect. To perform any of the functionality described herein, the processor 710 may execute one or more processor-executable instructions stored in one or more non-transitory computer-readable storage media (e.g., the memory 720), which may serve as non-transitory computer-readable storage media storing processor-executable instructions for execution by the processor 710.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided including with reference to FIGS. 3A, 3B, and 4. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Aspects of the technology described herein may have the following configurations:

(1) A system, comprising: a plurality of neuromuscular sensors, each of which is configured to record a time-series of neuromuscular signals from a surface of a user's body; at least one computer hardware processor; and at least one non-transitory computer-readable storage medium storing processor-executable instructions that, when executed by the at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

(2) The system of (1) wherein the plurality of neuromuscular source signals includes a first neuromuscular source signal and a second neuromuscular source signal, wherein the identifying comprises identifying a first set of one or more biological structures associated with the first neuromuscular source signal and a second set of one or more biological structures associated with the second neuromuscular source signal, and wherein the first set of biological structures is different from the second set of biological structures.

(3) The system of (2), wherein the first set of one or more biological structures includes at least one extensor muscle and wherein the second set of one or more biological structures includes at least one flexor muscle.

(4) The system of (2), wherein the first set of biological structures includes at least one muscle, at least one tendon, and/or at least one motor unit.

(5) The system of (2), wherein the processor-executable instructions further cause the at least one computer hardware processor to perform: providing at least some of the plurality of neuromuscular source signals as input to a trained statistical model different from the trained statistical classifier, the trained statistical model having at least a first input associated with the first set of one or more biological structures and second input associated with the second set of one or more biological structures, the providing comprising: providing the first neuromuscular source signal or data derived from the first neuromuscular source signal to the first input of the trained statistical model; and providing the second neuromuscular source signal or data derived from the second neuromuscular source signal to the second input of the trained statistical model; and controlling at least one device based, at least in part, on output of the trained statistical model.

(6) The system of (5), wherein controlling of the at least one device comprises: predicting, based on an output of the trained statistical model, whether an onset of a motor action will occur within a threshold amount of time; and when it is predicted that the onset of the motor action will occur within the threshold amount of time, sending a control signal to the at least one device prior to completion of the motor action by the user.

(7) The system of (5), wherein the trained statistical model is a recurrent neural network.

(8) The system of (1), wherein the plurality of neuromuscular sensors are arranged on a wearable device configured to be worn on or around a body part of the user.

(9) The system of (1), wherein the plurality of neuromuscular sensors comprises sensors selected from the group consisting of electromyography (EMG) sensors, mechanomyography (MMG) sensors, and sonomyography (SMG) sensors.

(10) The system of (1), wherein applying the source separation technique to the time-series of neuromuscular signals recorded by the plurality of neuromuscular sensors comprises applying independent components analysis (ICA) to the time-series of neuromuscular signals recorded by the plurality of neuromuscular sensors.

(11) The system of (1), wherein applying the source separation technique to the time-series of neuromuscular signals recorded by the plurality of neuromuscular sensors comprises applying non-negative matrix factorization (NNMF) to the time-series of neuromuscular signals recorded by the plurality of neuromuscular sensors.

(12) The system of (1), wherein the providing comprises: providing at least some of the corresponding mixing information or information derived from the corresponding mixing information as input to the trained statistical classifier.

(13) The system of (1), wherein the providing comprises: providing at least some of the plurality of neuromuscular source signals or information derived from the plurality of neuromuscular source signals as input to the trained statistical classifier.

(14) The system of (1), wherein the processor-executable instructions further cause the at least one hardware processor to perform: updating or retraining the trained statistical classifier at least in part by using information obtained from the time-series of neuromuscular signals recorded by the plurality of neuromuscular sensors.

(15) The system of (1), wherein the processor-executable instructions further cause the at least one hardware processor to perform: generating the trained statistical classifier using an supervised learning technique.

(16) The system of (1), wherein the identifying comprises: assigning a plurality of labels to the plurality of neuromuscular signals, wherein different labels in the plurality of labels indicate that different neuromuscular signals correspond to different sets of biological structures.

(17) The system of (1), wherein the identifying comprises: assigning a plurality of labels to the plurality of neuromuscular signals, wherein a first label in the plurality of labels identifies a first set of biological structures.

(18) A method, comprising using at least computer hardware processor to perform: applying a source separation technique to the time series of neuromuscular signals recorded by a plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

(19) At least one non-transitory computer-readable storage medium storing processor-executable instructions that, when executed by the at least one computer hardware processor, cause the at least one computer hardware processor to perform: applying a source separation technique to the time series of neuromuscular signals recorded by a plurality of neuromuscular sensors to obtain a plurality of neuromuscular source signals and corresponding mixing information; providing features, obtained from the plurality of neuromuscular source signals and/or the corresponding mixing information, as input to a trained statistical classifier and obtaining corresponding output; and identifying, based on the output of the trained statistical classifier, and for each of one or more of the plurality of neuromuscular source signals, an associated set of one or more biological structures.

(20) A system, comprising: a plurality of neuromuscular sensors, each of which is configured to record a time-series of neuromuscular signals from a surface of a user's body; at least one computer hardware processor; and at least one non-transitory computer-readable storage medium storing processor-executable instructions that, when executed by the at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

(21) The system of (20), wherein the plurality of neuromuscular source signals includes a first neuromuscular source signal and a second neuromuscular source signal, wherein the identifying comprises identifying a first set of one or more biological structures associated with the first neuromuscular source signal and a second set of one or more biological structures associated with the second neuromuscular source signal, and wherein the first set of biological structures is different from the second set of biological

(22) The system of (21), wherein the first set of one or more biological structures includes at least one extensor muscle and wherein the second set of one or more biological structures includes at least one flexor muscle.

(23) The system of (21), wherein the first set of biological structures includes at least one muscle, at least one tendon, and/or at least one motor unit.

(24) The system of (21), wherein the processor-executable instructions further cause the at least one computer hardware processor to perform: providing at least some of the plurality of neuromuscular source signals as input to a trained statistical model having at least a first input associated with the first set of one or more biological structures and second input associated with the second set of one or more biological structures, the providing comprising: providing the first neuromuscular source signal or data derived from the first neuromuscular source signal to the first input of the trained statistical model; and providing the second neuromuscular source signal or data derived from the second neuromuscular source signal to the second input of the trained statistical model; and controlling at least one device based, at least in part, on output of the trained statistical model.

(25) The system of (24), wherein controlling of the at least one device comprises:predicting, based on an output of the trained statistical model, whether an onset of a motor action will occur within a threshold amount of time; and when it is predicted that the onset of the motor action will occur within the threshold amount of time, sending a control signal to the at least one device prior to completion of the motor action by the user.

(26) The system of (24), wherein the trained statistical model is a recurrent neural network.

(27) The system of (19), wherein the plurality of neuromuscular sensors are arranged on a wearable device configured to be worn on or around a body part of the user.

(280 The system of (20), wherein the plurality of neuromuscular sensors comprises sensors selected from the group consisting of electromyography (EMG) sensors, mechanomyography (MMG) sensors, and sonomyography (SMG) sensors.

(29) The system of (20), wherein applying the source separation technique to the time-series of neuromuscular signals recorded by the plurality of neuromuscular sensors comprises applying independent components analysis (ICA) or non-negative matrix factorization (NNMF) to the time-series of neuromuscular signals recorded by the plurality of neuromuscular sensors.

(30) The system of (20), wherein applying the source separation technique to the time-series of neuromuscular signals recorded by the plurality of neuromuscular sensors comprises applying beamforming to the time-series of neuromuscular signals recorded by the plurality of neuromuscular sensors.

(31) The system of (20), wherein the aligning comprises: determining, using a cost function, a distance between the corresponding mixing information and the corresponding template mixing information.

(32) The system of (20), wherein the aligning comprises: determining, using a cost function, a distance between the plurality of neuromuscular source signals and the plurality of template neuromuscular source signals.

(33) The system of (32), wherein determining the distance between the plurality of neuromuscular source signals and the template neuromuscular source signals comprises: smoothing and/or rectifying the plurality of neuromuscular source signals to obtain first processed neuromuscular source signals; smoothing and/or rectifying the plurality of template neuromuscular source signals to obtain second processed neuromuscular source signals; and determining a distance between the first processed neuromuscular source signals and the second processed neuromuscular source signals.

(34) The system of (33), wherein determining the distance between the first processed neuromuscular source signals and the second processed neuromuscular source signals comprises: determining a first covariance of the first processed neuromuscular source signals; determining a second covariance of the second processed neuromuscular source signals; and calculating a distance between the first covariance and second covariance.

(35) A method, comprising: using at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

(36) At least one non-transitory computer-readable storage medium storing processor-executable instructions that, when executed by at least one computer hardware processor, cause the at least one computer hardware processor to perform: applying a source separation technique to the time series of neuromuscular signals recorded by the plurality of neuromuscular sensors to obtain a plurality of neuromuscular source signals and corresponding mixing information; aligning the plurality of neuromuscular source signals to a plurality of template neuromuscular source signals, the aligning comprising: determining, using a cost function, a distance between first features and second features, the first features obtained from the plurality of neuromuscular source signals and/or the corresponding mixing information, the second features obtained from the template neuromuscular source signals and/or corresponding template mixing information; and identifying, based on results of the aligning and for each of one or more of the plurality of neuromuscular source signals, an associated set of one or more biological structures.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system, comprising:
a plurality of neuromuscular sensors, each of which is configured to record a time-series of neuromuscular signals from a surface of a user's body;
at least one computer hardware processor; and
at least one non-transitory computer-readable storage medium storing processor-executable instructions that, when executed by the at least one computer hardware processor, cause the at least one computer hardware processor to perform:
applying a source separation technique to the time series of neuromuscular signals recorded by the plurality of neuromuscular sensors to obtain a plurality of neuromuscular source signals and corresponding mixing information;
providing features, obtained from the plurality of neuromuscular source signals and/or the corresponding mixing information, as input to a trained statistical classifier and obtaining corresponding output; and
identifying, based on the output of the trained statistical classifier, and for each of one or more of the plurality of neuromuscular source signals, an associated set of one or more biological structures.

2. The system of claim 1,
wherein the plurality of neuromuscular source signals includes a first neuromuscular source signal and a second neuromuscular source signal,
wherein the identifying comprises identifying a first set of one or more biological structures associated with the first neuromuscular source signal and a second set of one or more biological structures associated with the second neuromuscular source signal, and
wherein the first set of biological structures is different from the second set of biological structures.

3. The system of claim 2, wherein the first set of one or more biological structures includes at least one extensor muscle and wherein the second set of one or more biological structures includes at least one flexor muscle.

4. The system of claim 2, wherein the first set of biological structures includes at least one muscle, at least one tendon, and/or at least one motor unit.

5. The system of claim 2, wherein the processor-executable instructions further cause the at least one computer hardware processor to perform:
providing at least some of the plurality of neuromuscular source signals as input to a trained statistical model different from the trained statistical classifier, the trained statistical model having at least a first input associated with the first set of one or more biological structures and second input associated with the second set of one or more biological structures, the providing comprising:
providing the first neuromuscular source signal or data derived from the first neuromuscular source signal to the first input of the trained statistical model; and
providing the second neuromuscular source signal or data derived from the second neuromuscular source signal to the second input of the trained statistical model; and
controlling at least one device based, at least in part, on output of the trained statistical model.

6. The system of claim 5, wherein controlling of the at least one device comprises: predicting, based on an output of the trained statistical model, whether an onset
of a motor action will occur within a threshold amount of time; and
when it is predicted that the onset of the motor action will occur within the threshold amount of time, sending a control signal to the at least one device prior to completion of the motor action by the user.

7. The system of claim 5, wherein the trained statistical model is a recurrent neural network.

8. The system of claim 1, wherein the plurality of neuromuscular sensors are arranged on a wearable device configured to be worn on or around a body part of the user.

9. The system of claim 1, wherein the plurality of neuromuscular sensors comprises sensors selected from the group consisting of electromyography (EMG) sensors, mechanomyography (MMG) sensors, and sonomyography (SMG) sensors.

10. The system of claim 1, wherein applying the source separation technique to the time-series of neuromuscular signals recorded by the plurality of neuromuscular sensors comprises applying independent components analysis (ICA) to the time-series of neuromuscular signals recorded by the plurality of neuromuscular sensors.

11. The system of claim 1, wherein applying the source separation technique to the time-series of neuromuscular signals recorded by the plurality of neuromuscular sensors comprises applying non-negative matrix factorization (NNMF) to the time-series of neuromuscular signals recorded by the plurality of neuromuscular sensors.

12. The system of claim 1, wherein the providing comprises:
providing at least some of the corresponding mixing information or information derived from the corresponding mixing information as input to the trained statistical classifier.

13. The system of claim 1, wherein the providing comprises:
providing at least some of the plurality of neuromuscular source signals or information derived from the plurality of neuromuscular source signals as input to the trained statistical classifier.

14. The system of claim 1, wherein the processor-executable instructions further cause the at least one hardware processor to perform:
updating or retraining the trained statistical classifier at least in part by using information obtained from the time-series of neuromuscular signals recorded by the plurality of neuromuscular sensors.

15. The system of claim 1, wherein the processor-executable instructions further cause the at least one hardware processor to perform:
generating the trained statistical classifier using an supervised learning technique.

16. The system of claim 1, wherein the identifying comprises:
assigning a plurality of labels to the plurality of neuromuscular signals, wherein different labels in the plurality of labels indicate that different neuromuscular signals correspond to different sets of biological structures.

17. The system of claim 1, wherein the identifying comprises:
assigning a plurality of labels to the plurality of neuromuscular signals, wherein a first label in the plurality of labels identifies a first set of biological structures.

18. A method, comprising:
using at least computer hardware processor to perform:
applying a source separation technique to the time series of neuromuscular signals recorded by a plurality of neuromuscular sensors to obtain a plurality of neuromuscular source signals and corresponding mixing information;
providing features, obtained from the plurality of neuromuscular source signals and/or the corresponding mixing information, as input to a trained statistical classifier and obtaining corresponding output; and
identifying, based on the output of the trained statistical classifier, and for each of one or more of the plurality of neuromuscular source signals, an associated set of one or more biological structures.

19. At least one non-transitory computer-readable storage medium storing processor-executable instructions that, when executed by the at least one computer hardware processor, cause the at least one computer hardware processor to perform:
applying a source separation technique to the time series of neuromuscular signals recorded by a plurality of neuromuscular sensors to obtain a plurality of neuromuscular source signals and corresponding mixing information;
providing features, obtained from the plurality of neuromuscular source signals and/or the corresponding mixing information, as input to a trained statistical classifier and obtaining corresponding output; and
identifying, based on the output of the trained statistical classifier, and for each of one or more of the plurality of neuromuscular source signals, an associated set of one or more biological structures.

* * * * *